US005190958A

United States Patent [19]

Carter et al.

[11] Patent Number: 5,190,958

[45] Date of Patent: Mar. 2, 1993

[54] PIPERIDINE DERIVATIVES

[75] Inventors: Paul A. Carter, Sittingbourne; Surinder Singh, Chatham, both of England

[73] Assignee: Shell Research Limited, United Kingdom

[21] Appl. No.: 631,681

[22] Filed: Dec. 24, 1990

[30] Foreign Application Priority Data

Dec. 29, 1989 [GB] United Kingdom ................ 8929331

[51] Int. Cl.$^5$ ................ A61K 31/445; A61K 31/435; C07D 401/04; C07D 211/06

[52] U.S. Cl. ................................ 514/317; 514/235.5; 514/277; 514/315; 514/326; 514/330; 546/192; 546/194; 546/209; 546/210; 546/212; 546/214; 546/242; 546/245

[58] Field of Search ................ 544/124, 129; 546/194, 546/242, 245, 192, 209, 210, 212, 214; 514/277, 235.5, 317, 315, 326, 330

[56] References Cited

U.S. PATENT DOCUMENTS 3,352,871 11/1967 Cislak ................................ 546/226

FOREIGN PATENT DOCUMENTS 3614907 11/1987 Fed. Rep. of Germany .

OTHER PUBLICATIONS

Christine, Chemical Abstract, 96(19), 162553s, 1981.
Ueda et al., Chemical Abstract, 92(11), 94383b, 1979.

*Primary Examiner*—Mukund J. Shah
*Assistant Examiner*—Y. N. Gupta

[57] ABSTRACT

The invention provides piperidine derivatives of the general formula

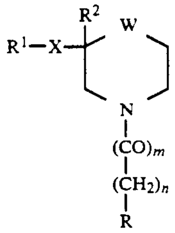

(I)

or an acid-addition salt or metal salt complex thereof, in which R represents a hydrogen atom or an optionally substituted alkyl, alkenyl, alkynyl, alkoxy, cycloalkyl, aryl, arylcarbonyl, heterocyclyl or heterocyclyloxy group; $R^1$ represents an optionally substituted alkyl, phenyl, benzyl or cycloalkyl group; $R^2$ represents a hydrogen atom or an optionally substituted alkyl group; one of W and X represents $—CH_2—$, $—CH_2CH_2—$ or —O—, the other of W and X being $—CH_2—$ or $—CH_2CH_2$ or X represents a single chemical bond; m is 0 or 1 and n represents an integer from 0 to 3; processes for their preparation; compositions containing such compounds and their use as fungicides.

7 Claims, No Drawings

PIPERIDINE DERIVATIVES

This invention relates to certain piperidine derivatives, a process for their preparation, compositions containing such compounds and their use as fungicides.

DE-A-3614907 discloses compounds of the general formula

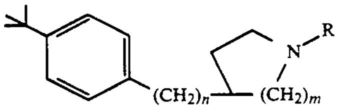

in which R represents a $C_{1-20}$ alkyl, $C_{2-20}$ alkoxyalkyl, $C_2$-$C_{20}$ hydroxyalkyl, $C_{3-12}$ cycloalkyl, $C_{4-20}$ alkylcycloalkyl, $C_{4-20}$ cycloalkylalkyl, aryl, haloaryl, $C_{7-}$•aralkyl, $C_{7-}$•haloaralkyl or $C_{7-}$•aryloxyalkyl group, m is 1 or 2 and n is 0 or 1, some of which are said to exhibit better activity than Fenpropimorph against certain phytopathogenic fungi. Compounds in which m is 2, that is, piperidine derivatives substituted at the 1- and 4- positions, and n is 0 are said to be especially preferred.

It has now been discovered that certain piperidine derivatives substituted at the 1- and 3- positions are highly active against certain phytopathogenic fungi. According to the present invention there is therefore provided a compound of the general formula

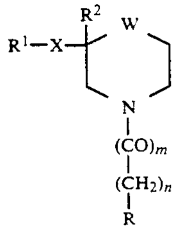

(I)

or an acid-addition salt or metal salt complex thereof, in which R represents a hydrogen atom or an optionally substituted alkyl, alkenyl, alkynyl, alkoxy, cycloalkyl, aryl, arylcarbonyl, heterocyclyl or heterocyclyloxy group; $R^1$ represents an optionally substituted alkyl, phenyl, benzyl or cycloalkyl group; $R^2$ represents a hydrogen atom or an optionally substituted alkyl group; one of W and X represents $—CH_2—$, $—CH_2CH_2—$ or $—O—$, the other of W and X being $—CH_2—$ or $—CH_2CH_2$, or X represents a single chemical bond; m is 0 or 1 and n represents an integer from 0 to 3.

When the compounds of this invention contain an alkyl, alkenyl or alkynyl substituent group, this may be linear or branched and may contain up to 12, preferably up to 6, carbon atoms. A cycloalkyl group may contain from 3 to 8, preferably 3 to 6, carbon atoms. An aryl group may be any aromatic hydrocarbon group, especially a phenyl or naphthyl group. A heterocyclyl group may be any saturated or unsaturated ring system containing at least one heteroatom, 5- and 6- membered rings being especially preferred.

When any of the foregoing substituents are designated as being optionally substituted, the substituent groups which are optionally present may be any one or more of those customarily employed in the development of pesticidal compounds and/or the modification of such compounds to influence their structure/activity, persistence, penetration or other property. Specific examples of such substituents include, for example, halogen atoms, nitro, cyano, hydroxyl, cycloalkyl, alkyl, haloalkyl, alkoxy, haloalkoxy, amino, alkylamino, dialkylamino, formyl, alkoxycarbonyl, carboxyl, alkanoyl, alkylthio, alkylsulphinyl, alkylsulphonyl, carbamoyl, alkylamido, phenyl, phenoxy and halophenoxy groups. When any of the foregoing substituents represents or contains an alkyl substituent group, this may be linear or branched and may contain up to 12, preferably up to 6, and especially up to 4, carbon atoms.

It is preferred that R represents a hydrogen atom or a $C_{1-12}$ alkyl, $C_{2-6}$ alkenyl, $C_{2-6}$ alkynyl, $C_{1-6}$ alkoxy, $C_{3-8}$ cycloalkyl, phenyl, naphthyl, phenylcarbonyl, heterocyclyl or heterocyclyloxy group, each group being optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino, formyl, $C_{1-4}$ alkoxycarbonyl, carboxyl, phenyl and halophenoxy groups.

More preferably, R represents a hydrogen atom or a $C_{1-12}$ alkyl, $C_{2-4}$ alkenyl, $C_{2-4}$ alkynyl, $C_{1-4}$ alkoxy, $C_{3-6}$ cycloalkyl, phenyl, naphthyl, phenylcarbonyl, heterocyclyl or heterocyclyloxy group, each group being optionally substituted by one or two substituents selected from halogen atoms, nitro, cyano, hydroxyl, $C_{1-4}$ alkyl, $C_{1-4}$ alkoxy, amino, $C_{1-4}$ alkoxycarbonyl, phenyl and halophenoxy groups.

It is preferred that $R^1$ represents a phenyl, benzyl or $C_{3-8}$ cycloalkyl group, each group being optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino, formyl, $C_{1-4}$ alkoxycarbonyl and carboxyl groups.

More preferably, $R^1$ represents a $C_{3-6}$ cycloalkyl group or a phenyl or benzyl group optionally substituted by a halogen atom, $C_{1-4}$ alkyl or $C_{1-4}$ alkoxy group.

Preferably, $R^2$ represents a hydrogen atom or a $C_{1-6}$, especially a $C_{1-4}$, alkyl group.

A particularly preferred sub-group of compounds of formula I is that in which R represents a hydrogen atom, methyl, ethyl, propyl, butyl, pentyl, hexyl, heptyl, octyl, nonyl, decyl, undecyl, dodecyl, hydroxymethyl, hydroxyethyl, hydroxypropyl, hydroxybutyl, ethoxyethyl, ethoxymethyl, diethoxyethyl, diethoxymethyl, ethoxycarbonylmethyl, dichlorophenoxyhydroxypropyl, ethenyl, propenyl, ethynyl, propynyl, butoxy, methoxyethoxy, cyclopentyl, cyclohexyl, phenyl, fluorophenyl, chlorophenyl, dichlorophenyl, bromophenyl, nitrophenyl, cyanophenyl, hydroxyphenyl, methylphenyl, butylphenyl, methoxyphenyl, aminophenyl, biphenylyl, naphthyl, hydroxynaphthyl, chlorophenylcarbonyl, pyridyl, imidazolyl, morpholinyl, furyl, tetrahydrofuryl, tetrahydropyranyl, thienyl or tetrahydropyranyloxy group; $R^1$ represents a phenyl, chlorophenyl, methylphenyl, propylphenyl, butylphenyl, methoxyphenyl, fluorobenzyl or cyclohexyl group; and $R^2$ represents a hydrogen atom or methyl group.

The compounds of formula I may form acid addition salts and metal salt complexes with a variety of acids and metal salts. However, acid addition salts with acids such as saccharin and mineral acids, particularly hydrochloric acid, are especially preferred.

It should also be appreciated that the compounds of formula I are capable of existing as different geometric isomers and diastereomers. The invention thus includes both the individual isomers and mixtures of such isomers.

The present invention also provides a process for the preparation of a compound of formula I as defined above or an acid-addition salt or metal salt complex thereof which comprises reacting a compound of the general formula

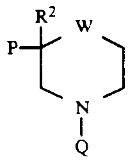

(II)

or an acid addition salt thereof, with a compound of the general formula $$Y—Z \quad (III)$$

in which, when P represents $—CH_2R^1$ or $—CH_2CH_2R^1$ and Q represents a hydrogen atom then Y represents $—(CO)_m(CH_2)_nR$ or when P represents —OH and Q represents $—(CO)_m(CH_2)_nR$ then Y represents $R^1$, Z represents a halogen atom and R, $R^1$, $R^2$, W, m and n are as defined above, in the presence of a base; if desired, when m and n are both 0, converting a compound of formula I in which R is nitrophenyl into a compound of formula I in which R is aminophenyl and, if desired, converting the compound of formula I in which R is aminophenyl into a compound of formula I in which R is chlorophenyl, bromophenyl, iodophenyl or cyanophenyl; and if desired, reacting the compound of formula I so obtained with a suitable acid or metal salt to form an acid-addition salt or metal salt complex thereof.

Conveniently, a compound of formula I in which X represents $—CH_2—$ or $—CH_2CH_2—$ is prepared by reacting a compound of formula II in which P is $—CH_2R^1$ or $—CH_2CH_2R^1$ and Q is a hydrogen atom with a compound of formula III in which Y is $—(CO)_m(CH_2)_nR$ and Z is a halogen, preferably fluorine, chlorine or bromine, atom in the presence of a base, such as sodium carbonate, potassium carbonate or triethylamine. Additionally, resulting compounds of formula I in which m is 1 may be converted into compounds of formula I in which m is 0 by reaction with a suitable reducing agent, such as lithium aluminium hydride.

Alternatively, a compound of formula I in which X represents —O— may be conveniently prepared by reacting a compound of formula II in which P is —OH and Q is $—(CO)_m(CH_2)_nR$ with a compound of formula III in which Y is $R^1$ and Z is a halogen, preferably fluorine, atom in the presence of a strong base, such as sodium hydride or sodium metal.

When m and n are both 0, a compound of formula I in which R is nitrophenyl may be converted into a compound of formula I in which R is aminophenyl by reaction with a suitable reducing agent, such as palladium on charcoal. The resulting compound of formula I in which R is aminophenyl may then be converted into a compound of formula in which R is chlorophenyl, bromophenyl, iodophenyl or cyanophenyl by reaction with sodium nitrite in the presence of an acid, such as hydrochloric acid, to form a diazonium salt followed by reaction with copper (I) chloride, copper (I) bromide, copper (I) iodide, or copper (I) cyanide in a Sandmeyer reaction.

The process of the invention is conveniently carried out in the presence of a solvent. Suitable solvents include ethers, particularly tetrahydrofuran, dimethylsulphoxide and dimethylformamide. The reaction is suitably carried out at a temperature of −20° to 180° C., the preferred reaction temperature being −5° to 165° C.

Compounds of formula II in which W represents $—CH_2—$ or $—CH_2CH_2—$ P represents $—CH_2R^1$ or $—CH_2CH_2R^1$ and Q represents a hydrogen atom may be conveniently prepared by reacting a compound of the general formula

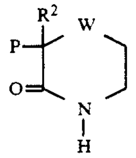

(IV)

in which P represents $—CH_2R^1$ or $—CH_2CH_2R^1$ and $R^2$ is as defined above, with a suitable reducing agent, such as lithium aluminium hydride.

Compounds of formula IV may be prepared by reacting a compound of the general formula

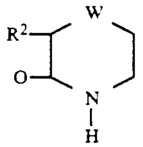

(V)

in which $R^2$ is as defined above and W represents $—CH_2—$ or $—CH_2CH_2—$, with a compound of the general formula $$P—L \quad (VI)$$

in which P represents $—CH_2R^1$ or $—CH_2CH_2R^1$ and L is a leaving group, preferably a halogen, especially a bromine, atom, in the presence of a suitable base, such as butyl lithium.

Compounds of formula II in which P represents —OH and Q represents $—(CO)_m(CH_2)_nR$ may be conveniently prepared by reacting a compound of the general formula

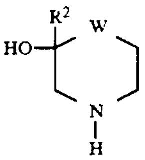

(VII)

in which $R^2$ and W are as defined above, with a compound of the general formula $$R(CH_2)_n(CO)_mL^1 \quad (VIII)$$

in which R is as defined above and $L^1$ is a leaving group, preferably a halogen, especially a chlorine or bromine, atom, in the presence of a suitable base, such as sodium carbonate, potassium carbonate or triethylamine.

Compounds of formula VII may be prepared by the method of J. H. Biel, H. L. Friedman, H. A. Leiser and E. P. Sprengler, J.Am. Chem. Soc., 1952, 74, 1485.

Compounds of formula II in which W represents —O—, P represents $-CH_2R^1$ or $-CH_2CH_2R^1$ and Q represents a hydrogen atom, or acid addition salts thereof, may be conveniently prepared by reacting a compound of the general formula

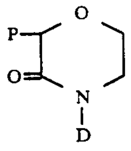

(IX)

in which P represents $-CH_2R^1$ or $-CH_2CH_2R^1$, D represents a protecting group, such as a benzyl group, and $R^1$ is as defined above, with a reagent that removes the protecting group D, such as ethyl chloroformate or chloroethyl chloroformate.

Compounds of formula IX may be prepared by reacting a compound of the general formula

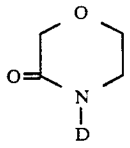

(X)

in which D is as defined above, with a compound of formula VI, as defined above, in the presence of a suitable base, such as lithium diisopropylamide.

Compounds of formula X may be prepared by reacting a compound of the general formula $$D{-}NH{-}CH_2CH_2OH \quad (XI)$$

in which D is as defined above, with a compound of the general formula $$Hal{-}CH_2COOCH_2CH_3 \quad (XII)$$

in which Hal represents a chlorine or bromine atom, in the presence of a suitable base, such as sodium hydride.

Compounds of formula III, V, VI, VIII. XI and XII are known compounds or can be prepared by processes analogous to known processes.

The compounds of general formula I have been found to have fungicidal activity. Accordingly, the invention further provides a fungicidal composition which comprises a carrier and, as active ingredient, a compound of formula I or an acid-addition salt or metal salt complex thereof as defined above. A method of making such a composition is also provided which comprises bringing a compound of formula I as defined above, or an acid-addition salt or metal salt complex thereof, into association with at least one carrier. Such a composition may contain a single compound or a mixture of several compounds of the present invention. It is also envisaged that different isomers or mixtures of isomers may have different levels or spectra of activity and thus compositions may comprise individual isomers or mixtures of isomers.

A composition according to the invention preferably contains from 0.5 to 95% by weight of active ingredient.

A carrier in a composition according to the invention is any material with which the active ingredient is formulated to facilitate application to the locus to be treated, which may for example be a plant, seed or soil, or to facilitate storage, transport or handling. A carrier may be a solid or a liquid, including a material which is normally gaseous but which has been compressed to form a liquid, and any of the carriers normally used in formulating fungicidal compositions may be used.

Suitable solid carriers include natural and synthetic clays and silicates, for example natural silicas such as diatomaceous earths; magnesium silicates, for example talcs; magnesium aluminium silicates, for example attapulgites and vermiculites; aluminium silicates, for example kaolinites, montmorillonites and micas; calcium carbonate; calcium sulphate; ammonium sulphate; synthetic hydrated silicon oxides and synthetic calcium or aluminium silicates; elements, for example carbon and sulphur; natural and synthetic resins, for example coumarone resins, polyvinyl chloride, and styrene polymers and copolymers; solid polychlorophenols; bitumen; waxes, for example beeswax, paraffin wax, and chlorinated mineral waxes; and solid fertilisers, for example superphosphates.

Suitable liquid carriers include water; alcohols, for example isopropanol and glycols; ketones, for example acetone, methyl ethyl ketone, methyl isobutyl ketone and cyclohexanone; ethers; aromatic or araliphatic hydrocarbons, for example benzene, toluene and xylene; petroleum fractions, for example, kerosine and light mineral oils; chlorinated hydrocarbons, for example carbon tetrachloride, perchloroethylene and trichloroethane. Mixtures of different liquids are often suitable.

Fungicidal compositions are often formulated and transported in a concentrated form which is subsequently diluted by the user before application. The presence of small amounts of a carrier which is a surface-active agent facilitates this process of dilution. Thus preferably at least one carrier in a composition according to the invention is a surface-active agent. For example the composition may contain at least two carriers, at least one of which is a surface-active agent.

A surface-active agent may be an emulsifying agent, a dispersing agent or a wetting agent; it may be nonionic or ionic. Examples of suitable surface-active agents include the sodium or calcium salts of polyacrylic acids and lignin sulphonic acids; the condensation products of fatty acids or aliphatic amines or amides containing at least 12 carbon atoms in the molecule with ethylene oxide and/or propylene oxide; fatty acid esters of glycerol, sorbitol, sucrose or pentaerythritol; condensates of these with ethylene oxide and/or propylene oxide; condensation products of fatty alcohol or alkyl phenols, for example p-octylphenol or p-octylcresol, with ethylene oxide and/or propylene oxide; sulphates or sulphonates of these condensation products; alkali or alkaline earth metal salts, preferably sodium salts, of sulphuric or sulphonic acid esters containing at least 10 carbon atoms in the molecule, for example sodium lauryl sulphate, sodium secondary alkyl sulphates, sodium salts of sulphonated castor oil, and sodium alkylaryl sulphonates such as dodecylbenzene sulphonate; and polymers of ethylene oxide and copolymers of ethylene oxide and propylene oxide.

The compositions of the invention may for example be formulated as wettable powders, dusts, granules, solutions, emulsifiable concentrates, emulsions, suspension concentrates and aerosols. Wettable powders usually contain 25, 50 or 75% w of active ingredient and usually contain in addition to solid inert carrier, 3-10% w of a dispersing agent and, where necessary, 0-10% w of stabiliser(s) and/or other additives such as penetrants or stickers. Dusts are usually formulated as a dust concentrate having a similar composition to that of a wettable powder but without a dispersant, and may be diluted in the field with further solid carrier to give a composition usually containing ½-10% w of active ingredient. Granules are usually prepared to have a size between 10 and 100 BS mesh (1.676-0.152 mm), and may be manufactured by agglomeration or impregnation techniques. Generally, granules will contain ½-75% w active ingredient and 0-10% w of additives such as stabilisers, surfactants, slow release modifiers and binding agents. The so-called "dry flowable powders" consist of relatively small granules having a relatively high concentration of active ingredient. Emulsifiable concentrates usually contain, in addition to a solvent and, when necessary, co-solvent, 1-50% w/v active ingredient, 2-20% w/v emulsifiers and 0-20% w/v of other additives such as stabilisers, penetrants and corrosion inhibitors. Suspension concentrates are usually compounded so as to obtain a stable, non-sedimenting flowable product and usually contain 10-75% w active ingredient, 0.5-15% w of dispersing agents, 0.1-10% w of suspending agents such as protective colloids and thixotropic agents, 0-10% w of other additives such as defoamers, corrosion inhibitors, stabilisers, penetrants and stickers, and water or an organic liquid in which the active ingredient is substantially insoluble; certain organic solids or inorganic salts may be present dissolved in the formulation to assist in preventing sedimentation or as antifreeze agents for water.

Aqueous dispersions and emulsions, for example compositions obtained by diluting a wettable powder or a concentrate according to the invention with water, also lie within the scope of the invention. The said emulsions may be of the water-in-oil or of the oil-in-water type, and may have a thick 'mayonnaise' like consistency.

The composition of the invention may also contain other ingredients, for example other compounds possessing herbicidal, insecticidal or fungicidal properties.

Of particular interest in enhancing the duration of the protective activity of the compounds of this invention is the use of a carrier which will provide a slow release of the fungicidal compounds into the environment of the plant which is to be protected. Such slow-release formulations could, for example, be inserted in the soil adjacent to the roots of a vine plant, or could include an adhesive component enabling them to be applied directly to the stem of a vine plant.

The invention still further provides the use as a fungicide of a compound of the general formula I as defined above or an acid-addition salt or metal salt complex thereof or a composition as defined above, and a method for combating fungus at a locus, which comprises treating the locus, which may be for example plants subject to or subjected to fungal attack, seeds of such plants or the medium in which such plants are growing or are to be grown, with such a compound or composition.

The present invention is of wide applicability in the protection of crop plants against fungal attack. Typical crops which may be protected include vines, grain crops such as wheat and barley, rice and tomatoes. The duration of protection is normally dependent on the individual compound selected, and also a variety of external factors, such as climate, whose impact is normally mitigated by the use of a suitable formulation.

The invention is further illustrated by the following examples.

EXAMPLE 1

Preparation of N-2'-(3-thienyl)ethyl-3-phenylmethylpiperidine ($R$=thien-3-yl; $R^1$=phenyl; $R^2$=hydrogen; $W=-CH_2-$; $X=-CH_2-$; $m=0$; $n=2$)

(i) Preparation of 3-phenylmethylpiperid-2-one

To a stirred solution of 2-piperidone (40 g, 0.404 mol) in tetrahydrofuran (800 ml) at 0° C. was added, over a period of 2 hours, n-butyl lithium (2.5 M in hexane, 356 ml, 0.889 mol). The reaction was cooled to −40° C. and a solution of benzyl bromide (48 ml, 0.404 mol) in tetrahydrofuran (200 ml) was added dropwise over a period of 2 hours. The reaction was allowed to warm slowly to room temperature and stirred for 12 hours. Water (100 ml) and saturated aqueous ammonium chloride (100 ml) were added and the aqueous phase separated and extracted with ethyl acetate (3×100 ml). The combined organic phases were washed with brine (200 ml), dried with sodium sulphate and evaporated in vacuo. The resulting solid was recrystallised from toluene to give the desired product as white needles (41.2 g), m.pt. 120°-123° C. Low resolution mass spectroscopy revealed the mass/charge ratio of the parent molecule ion, $M^+$, to be 190 thereby confirming the molecular of the product to be 190.

Analysis: Calc.: C: 76.2; H: 8.0; N: 7.4%.
Found: C: 76.0; H: 7.8; N: 7.6%.

(ii) Preparation of 3-phenylmethylpiperidine

To an ice cooled suspension of lithium aluminium hydride (18.6 g, 0.49 mol) in tetrahydrofuran (930 ml) was added portionwise, with stirring, the 3-phenylmethylpiperid-2-one (23.1 g, 0.122 mol) obtained in (i). The reaction mixture was then heated under reflux for 5 hours, cooled and worked up with saturated aqueous sodium sulphate. The reaction mixture was then filtered through a pad of "Hyflo" (Trade Mark: diatomaceous earth) and the pad washed well with ethyl acetate. The solvent was then evaporated in vacuo and the residue distilled at 0.05 mm Hg, b.pt. 77°-80° C., to give the desired product as a clear colourless oil (16.1 g), $M^+$ found 176.

Analysis: Calc.: C: 82.2; H: 9.8; N: 8.0%.
Found: C: 81.9; H: 9.9; N: 8.3%.

(iii) Preparation of N-2'-(3-thienyl)ethyl-3-phenylmethylpiperidine

A mixture of the 3-phenylmethylpiperidine (1 g, 5.71 mmol) obtained in (ii), 2-(3'-thiophenyl)-1-bromoethane (1.09 g, 5.71 mmol) and potassium carbonate (2.37 g, 17.1 mmol) in tetrahydrofuran (50 ml) was heated, with stirring, under reflux for 2 days. The reaction mixture was then cooled and poured into water (20 ml). The aqueous phase was then extracted with ethyl acetate (2×10 ml) and the combined organic phases washed with brine (10 ml) and dried with sodium sulphate. The solvent was then evaporated in vacuo and the residue purified by flash column chromatography on silica gel using 45:4:1 hexane: ethyl acetate: triethylamine as eluant to give N-2'-(3-thiophenyl)ethyl-3-phenylmethylpiperidine as a clear colourless oil (1.36 g), $M^+$ found 286.

Analysis: Calc.: C: 75.7; H: 8.1; N: 4.9%.

Found: C: 75.5; H: 7.9; N: 5.0%.

EXAMPLE 2

Preparation of 3-phenylmethyl-N-(4'-methoxyphenyl) acetylpiperidine ($R$=4-methoxyphenyl; $R^1$=phenyl; $R^2$=hydrogen; $W$=—$CH_2$—; $X$=—$CH_2$—; $m$=1; $n$=1)

To a solution of the 3-phenylmethylpiperidine (1.75 g, 10 mmol) obtained in Example 1 (ii) and triethylamine (2.1 ml, 15 mmol) in tetrahydrofuran (10 ml) at 0° C. was added dropwise a solution of 4-methoxyphenylacetyl chloride (2.21 g, 12 mmol) in tetrahydrofuran (10 ml). The resultant mixture was stirred for 2 hours and the precipitate filtered off. The filtrate was then washed with saturated aqueous sodium bicarbonate (5 ml), dried with sodium sulphate and evaporated in vacuo. The residue was purified by flash column chromatography on silica gel using 1:1 then 2:1 ethyl acetate: hexane as eluant to give 3-phenylmethyl-N-(4'-methoxyphenyl-)acetylpiperidine as a light yellow syrup (2.23 g), $M^+$ found: 324.

Analysis: Calc.: C: 78.0; H: 7.8; N: 4.3%.

Found: C: 76.7; H: 7.5; N: 4.5%.

EXAMPLE 3

Preparation of N-2'-(4-methoxyphenyl)ethyl-3-phenylmethylpiperidine ($R$=4-methoxyphenyl; $R^1$=phenyl; $R^2$=hydrogen; $W$=—$CH_2$—; $X$=—$CH_2$—; $m$=0; $n$=2

To a stirred suspension of lithium aluminium hydride (0.35 g, 9.28 mmol) in tetrahydrofuran (10 ml) was added dropwise a solution of the 3-phenylmethyl-N-(4'-methoxyphenyl)acetylpiperidine (1.5 g, 4.64 mmol) obtained in Example 2 in tetrahydrofuran (10 ml). The reaction mixture was then heated under reflux for 20 hours, cooled and worked up with saturated aqueous sodium sulphate. The reaction mixture was then filtered through a pad of "Hyflo" (Trade Mark: diatomaceous earth) and the pad washed well with ethyl acetate. The filtrate was then evaporated in vacuo and the residue purified by flash column chromatography on silica gel using 83:15:2 hexane:ethyl acetate:triethylamine as eluant to give N-2'-(4-methoxyphenyl)ethyl-3-phenylmethylpiperidine as a clear colourless oil (1.15 g), $M^+$ found: 310.

Analysis: Calc.: C: 81.5 H: 8.8 N: 4.5%.

Found: C: 81.5 H: 8.9 N: 4.9%.

EXAMPLE 4

Preparation of 3-phenoxy-N-phenylmethylpiperidine ($R$=phenyl; $R^1$=phenyl; $R^2$=hydrogen; $W$=—$CH_2$—; $X$=—O—; $m$=0; $n$=1)

(i)Preparation of 3-hydroxy-N-phenylmethylpiperidine

A mixture of 3-hydroxypiperidine (6 g, 59.3 mmol), benzyl bromide (10.1 g, 59.3 mmol) and potassium carbonate (25 g) in tetrahydrofuran (150 ml) was heated, with stirring, under reflux for 3 days. The reaction mixture was then cooled and poured into water (100 ml). The aqueous phase was then extracted with ethyl acetate (3×20 ml) and the combined organic phases washed with brine (50 ml) and dried with sodium sulphate. The solvent was then evaporated in vacuo and the residue purified by flash column chromatography on silica gel using 35:14:1 hexane: ethyl acetate: triethylamine as eluant to give the desired product as a colourless oil (9 g), $M^+$ found: 192.

Analysis: Calc.: C: 75.3; H: 8 9; N: 7.3%.

Found: C: 75.7; H: 9.6; N: 7.4%.

(ii)Preparation of 3-phenoxy-N-phenylmethylpiperidine

To sodium hydride (60% dispersion in mineral oil, 0.47 g, 11.7 mmol) in dimethylformamide (20 ml) was added the 3-hydroxy-N-phenylmethylpiperidine (1.5 g, 7.8 mmol) obtained in (i) in dimethylformamide (10 ml). The reaction mixture was heated at 50° C. until effervescence ceased and then fluorobenzene (1.1 ml, 1.1 g) was added and the reaction mixture heated for 2 days at 75° C. The reaction mixture was then cooled, water (600 ml) added and extracted with toluene (4×70 ml). The combined extracts were then dried with sodium sulphate and evaporated in vacuo and the residue purified by flash chromatography on silica gel using 70:28:2 hexane: ethyl acetate: triethylamine as eluant to give 3-phenoxy-N-phenylmethylpiperidine as a colourless oil (1.3 g), $M^+$ found: 268.

Analysis: Calc.: C: 80.9; H 7.9; N: 5.2%.

Found: C: 80.9; H: 7.8: N: 5.3%.

EXAMPLE 5

Preparation of N-benzyl-3-(2'-phenyl)ethyl piperidine ($R$=phenyl; $R^1$=phenyl; $R^2$=hydrogen; $W$=—$CH_2$—; $X$=—$CH_2CH_2$—; $m$=0; $n$=1)

(i) Preparation of 3-(2'-phenyl)ethyl piperid-2-one

A solution of n-butyl lithium in hexane (2.4 M, 190 ml, 0.48 mol) was added, with mechanical stirring, dropwise over a period of 90 minutes to a solution of 2-piperidone (21.4 g, 0.22 mol) in tetrahydrofuran (430 ml) at 0° C. The mixture was stirred for 1 hour and then cooled to −40° C. A solution of 2'-bromoethylbenzene (40.0 g, 0.22 mol) in tetrahydrofuran (100 ml) was then added dropwise over a period of 1 hour. The reaction mixture was then allowed to warm slowly to room temperature and stirred for 3 days. Addition of saturated aqueous ammonium chloride (200 ml) and water (200 ml) was followed by extraction of the aqueous phase with ethyl acetate (3×200 ml). The combined organic phases were washed with brine (250 ml), dried with sodium sulphate and evaporated in vacuo to give an oil. Purification by flash column chromatography upon silica gel using initially petroleum ether then methanol: ethyl acetate: triethylamine (49:49:2) as eluant gave the desired product as a white solid, 34.2 g, M.pt. 96°–98° C. (from hexane), $M^+$ found: 203.

Analysis: Calc.: C: 76.8; H: 8.4; N: 6.9%.

Found: C: 76.1; H: 8.5; N: 7.1%.

(ii) Preparation of 3-(2'-phenyl)ethyl piperidine

The 3-(2'-phenyl)ethyl piperid-2-one (31 g, 0.15 mol) obtained in (i) was added portionwise to a stirred suspension of lithium aluminium hydride (23.1 g, 0.61 mol) in tetrahydrofuran (1000 ml). The reaction was heated under reflux for 24 hours, cooled to 5° C. and worked up with saturated aqueous sodium sulphate. The resulting suspension was filtered through Hyflo (Trade Mark: diatomaceous earth) and the pad washed well with ethyl acetate. Evaporation of the filtrate in vacuo followed by flash column chromatography upon silica gel using ethyl acetate: methanol: triethylamine (49:49:2) as eluant afforded the desired product as a clear, colourless oil, 23.7 g, $M^+$ found: 189.

Analysis: Calc.: C: 82.5; H: 10.0; N: 7.4%.

Found: C: 81.1; H: 10.0; N: 7.9%.

(iii)Preparation of N-benzyl-3-(2'-phenyl)ethyl piperidine

A mixture of the 3-(2'-phenyl)ethyl piperidine (2.0 g, 10.5 mmol) obtained in (ii), benzyl bromide (1.8 g, 10.5 mmol) and potassium carbonate 4.35 g, 31.5 mmol) in tetrahydrofuran (50 ml) were heated under reflux, with stirring, for 17 hours. The reaction was then cooled and water (100 ml) added. The aqueous phase was extracted with ethyl acetate (3×50 ml) and the combined organic phases washed with brine, dried with sodium sulphate and evaporated in vacuo. The resulting oil was purified by flash column chromatography upon silica gel using hexane: triethylamine (98:2) as eluant to afford the desired product as a clear colourless oil, 2.2 g, M+ found: 279.

Analysis: Calc.: C: 86.0; H: 9.0; N: 5.0%.

Found: C: 86.2; H: 9.2; N: 5.4%.

EXAMPLE 6

(Preparation of N-(4-chlorobenzyl)-3-phenylmethyl hexahydroazepine ($R$=4-chlorophenyl; $R^1$=phenyl; $R^2$=hydrogen; $W$=—$CH_2CH_2$—; $X$=—$CH_2$—; $m$=0; $n$=1)

(i) Preparation of 3-phenylmethylhexahydroazepin-2-one

A solution of n-butyl lithium in hexane (2.5 M, 178 ml, 0.444 mol) was added dropwise to a mechanically stirred solution of hexahydroazepin-2-one (22.8 g, 0.202 mol) in tetrahydrofuran (400 ml) over a period of 90 minutes at 0° C. The solution was stirred for 3 hours and then cooled to −50° C. Benzyl bromide (24 ml, 0.202 mol) in tetrahydrofuran (100 ml) was then added dropwise over a period of 1 hour and the reaction mixture allowed to warm slowly to room temperature and stirred for 15 hours. Addition of water (100 ml) and saturated aqueous ammonium chloride (100 ml) was followed by extraction of the aqueous phase with ethyl acetate (3×100 ml). The combined organic phases were washed with brine, dried with sodium sulphate and evaporated in vacuo. Flash column chromatography upon silica gel of the resulting oily solid using ethyl acetate: methanol (25:1) as eluant afforded a solid which was recrystallised from benzene/hexanes to give the desired product as an off white solid, 10.3 g, M.pt. 99°–104° C., M+ found: 203.

Analysis: Calc: C: 76.8; H: 8.4; N: 6.9%.

Found: C: 76.9; H: 8.4; N: 6.8%.

(ii) Preparation of 3-phenlmethylhexahydroazepine

The 3-phenylmethylhexahydroazepin-2-one (9.25 g, 45.6 mmol) obtained in (i) was added portionwise to a stirred suspension of lithium aluminium hydride (5.19 g, 137 mmol) in tetrahydrofuran (300 ml). The reaction mixture was then heated under reflux for 7 hours, cooled and worked up with saturated aqueous sodium sulphate. The resulting suspension was filtered through Hyflo (Trade mark: diatomaceous earth) with the pad washed well with ethyl acetate. Evaporation of the filtrate followed by Kugelrohr distillation at 0.05 mm Hg, oven temperature 110° C. gave the desired product as a clear, colourless oil, 6.8 g, M+ found: 189.

Analysis: Calc: C: 82.5; H: 10.1; N: 7.4%.

Found: C: 81.4; H: 10.4; N: 6.8%.

(iii)Preparation of N-(4-chlorobenzyl)-3-phenylmethyl-hexahydroazepine

A suspension of potassium carbonate (2.37 g, 17.1 mmol) in a solution of the 3-phenylmethylhexahydroazepine (1.08 g, 5.71 mmol) obtained in (ii) and 4-chlorobenzyl chloride (0.92 g, 5.71 mmol) in tetrahydrofuran (50 ml) was heated under reflux, with stirring, for 1 day. The reaction mixture was then cooled and water (25 ml) added. The aqueous phase was extracted with ethyl acetate (3×20 ml) and the combined organic phases washed with brine (20 ml). After drying with sodium sulphate and evaporation in vacuo, the resulting oil was purified by flash column chromatography upon silica gel using hexane: ethyl acetate: triethylamine (70:28:2) as eluant to afford the desired product as a clear, colourless oil, 1.21 g, M+ found: 313/315.

Analysis: Calc: C: 76.5; H: 7.7; N: 4 5%.

Found: C: 76.8; H: 7.7; N: 4.9%.

EXAMPLE 7

Preparation of N-(4-bromobenzyl)-2-(4-tert-butylphenylmethyl) morpholine ($R$=4-bromophenyl; $R^1$=4-tert-butylphenyl; $R^2$=hydrogen; $W$=—O—; $X$=—$CH_2$—; $m$=0; $n$=1)

(i) Preparation of N-benzyl morpholin-3-one

A solution of N-benzyl ethanolamine (60.4 g, 0.40 mol) in toluene (400 ml) was added over a period of 1 hour to a mechanically stirred suspension of sodium hydride (60% dispersion in mineral oil, 17.6 g, 0.44 mol) in toluene (800 ml). The reaction was heated under reflux for 2 hours before being cooled to room temperature and a solution of ethyl bromoacetate (44.4 ml, 0.40 mol) in toluene (600 ml) added over a period of 30 minutes. The reaction was then heated under reflux for 15 hours before being cooled to room temperature and water (1000 ml) added. The aqueous phase was extracted with ethyl acetate (3×200 ml) and the combined organic phases washed with brine (500 ml), dried with sodium sulphate and evaporated in vacuo. The resulting oil was purified by flash column chromatography upon silica gel using ethyl acetate: hexanes: triethylamine (70:28:2) as eluant affording the desired product as a yellow oil, 32 g, M+ found: 191.

Analysis: Calc: C: 69.1; H: 6.9; N: 7.3%.

Found: C: 68.2; H: 7.1; N: 6.9%.

(ii) Preparation of N-benzyl-2-(4-tert-butylphenylmethyl)morpholin-3-one

A solution of the N-benzyl morpholin-3-one (4.46 g, 23.4 mmol) obtained in (i) in tetrahydrofuran (25 ml) was added dropwise over a period of 15 minutes to a solution of lithium diisopropylamide (28.0 mmol [prepared from diisopropylamine (3.93 ml, 28.0 mmol) and n-butyl lithium (2.5 M in hexanes, 11.2 ml, 28.0 mmol)]) in tetrahydrofuran (50 ml), with stirring, at −78° C. The resulting solution was stirred for 45 minutes and then 4-tert-butylbenzyl bromide (6.0 ml, 32.7 mmol) in tetrahydrofuran (25 ml) was added dropwise over a period of 10 minutes. The reaction mixture was stirred for 90 minutes and then warmed to room temperature. Addition of water (25 ml) and saturated aqueous ammonium chloride (25 ml) was followed by extraction of the aqueous phase by ethyl acetate (3×20 ml). The combined organic phases were washed with brine (20 ml), dried with sodium sulphate and evaporated in vacuo. Flash column chromatography of the resulting oil upon silica gel using hexane: ethyl acetate (1:1) as eluant afforded the desired product as a clear, faintly yellow oil, 5.29 g, M+ found: 337.

Anaylsis: Calc: C: 78.3; H: 8.1; N: 4.2%.

Found: C: 76.6; H: 8.0; N: 4.4%.

(iii) 2-(4-tert-butylphenylmethyl)morpholine, hydrochloride

1-Chloroethyl chloroformate (2.98 ml, 27.7 mmol) was added in a steady stream to a stirred solution of the N-benzyl-2-(4-tert-butylphenylmethyl)morpholine (8.94 g, 27.7 mmol) obtained in (ii) in 1,2-dichloroethane (100 ml) at 0° C. The reaction was stirred for 20 minutes and then heated under reflux for 135 minutes before cooling and evaporation in vacuo. Methanol (100 ml) was then added and the reaction heated under reflux for 1 hour before cooling, evaporation in vacuo and dissolution in chloroform (about 200 ml). This solution was washed with saturated aqueous sodium hydrogen carbonate (20 ml), dried with sodium sulphate and evaporated in vacuo. The resulting gummy solid was recrystallised from chloroform/diethyl ether to afford the desired product as a white solid, 1.5 g, M.pt. 190°-193° C., M+—HCl found: 233.

Analysis: Calc: C: 66.8; H: 9.0; N: 5.2%.

Found: C: 66.2; H: 8.7; N: 5.0%.

(iv) Preparation of N-(4-bromobenzyl)-2-(4-tert-butylphenylmethyl)morpholine

A mixture of the (4-tert-2-butylphenylmethyl)morpholine hydrochloride (1 g, 3.75 mmol) obtained in (iii), 4-bromobenzyl bromide (1.07 g, 4.3 mmol) and potassium carbonate (1.78 g, 12.9 mmol) in dimethylformamide (50 ml) was heated at 110°-130° C., with stirring, for 3 days. The reaction was then cooled and water (50 ml) added. This solution was extracted with ethyl acetate (5×20 ml). The combined organic extracts were washed with brine (20 ml), dried with sodium sulphate and evaporate in vacuo. Flash column chromatography upon silica gel of the resulting oil using hexanes: ethyl acetate: triethylamine (90:8:2) afforded the desired product as a faintly yellow oil, 1.50 g, M+ found: 401/403.

Analysis: Calc: C: 65.7; H: 7 0; N: 3.5%.

Found: C: 65.6; H: 6.5; N: 3.6%.

EXAMPLE 8

Preparation of 3-(4-tert-butylphenylmethyl)-1-(4-nitrophenyl)piperidine ($R$=4-nitrophenyl; $R^1$=4-tert-butylphenyl; $R^2$=hydrogen; W=—$CH_2$—; X=—$CH_2$—; m=0; n=0)

A solution of para-fluoronitrobenzene (18.1 g, 128 mmol) in dimethylsulphoxide (150 ml) was added to a suspension of potassium carbonate (17.7 g, 128 mmol) in a solution of 3-(4-tert-butylphenylmethyl) piperidine (29.7 g, 128 mmol), prepared by a method analogous to that given in Example 1 (i) and (ii), in dimethylsulphoxide (300 ml) with stirring. The reaction was heated at 100° C. for 26 hours and then cooled. The reaction was then poured into water (1 liter) and extracted with ethyl acetate (3×500 ml). The combined organic extracts were dried with magnesium sulphate and evaporated. The resulting solid was then recrystallised from ethyl acetate/petroleum ether to yield the desired product as yellow crystals, 35.0 g, (Yield: 78%), M.pt. 92°-94° C., M+ found: 352.

Analysis: Calc: C: 74.9; H: 6.8; N: 9.5%.

Found: C: 73.2; H: 7.0; N: 9.6%.

EXAMPLE 9

Preparation of 3-(4-tert-butylphenylmethyl)-1-(4-aminophenyl)piperidine ($R$=4-aminophenyl; $R^1$=4-tert-butylphenyl; $R^2$=hydrogen; W=—$CH_2$—; X=—$CH_2$—; m=0; n=0)

A solution of the 3-(4-tert-butylphenylmethyl)-1-(4-nitrophenyl)piperidine (2.0 g, 5.7 mmol) obtained in Example 8 in ethyl acetate (250 ml) and ethanol (250 ml) containing 5% palladium on charcoal was hydrogenated at approximately 3 atmospheres until uptake ceased. The reaction was then filtered through Celite (Trade Mark: diatomaceous earth) and evaporated to yield the desired product as a thick oil, 1.8 g, (Yield: 98%), M+ found: 322.

Analysis: Calc: C: 81.9; H: 9.4; N 8.7%.

Found: C: 80 3; H: 9.6; N 8.2%.

EXAMPLE 10

Preparation of 3-(4-t-butylphenylmethyl)-1-(4-chlorophenyl)piperidine ($R$=4-chlorophenyl; $R^1$=4-tert-butylphenyl; $R^2$=hydrogen; W=—$CH_2$—; X=—$CH_2$—; m=0; n=0)

To a solution of the 3-(4-tert-butylphenylmethyl)-1-(4-aminophenyl)piperidine (5.5 g, 17.0 mmol) obtained in Example 9 in concentrated hydrochloric acid (10 ml) and water (10 ml) at 0° C. was added over 15 minutes a solution of sodium nitrite (1.38 g, 20.0 mmol) in water (10 ml). After 30 minutes an aliquot of the resulting solution (18 ml) was poured into a solution of copper (I) chloride (2.34 g) in concentrated hydrochloric acid (20 ml) and the reaction warmed to room temperature. After 2 hours the reaction was heated at 60° C. for 10 hours and then cooled and partitioned between water and chloroform. The aqueous phase was extracted with chloroform and the combined organic phases dried with magnesium sulphate and evaporated. The resulting solid was chromatographed upon silica gel using chloroform as eluant to yield the desired product as a light orange solid, 2.71 g, (Yield: 93%), M.pt. 102°-104° C., M+ found 341/343.

Analysis: Calc: C 77.3; H 8.3; N 4.1%.

Found: C 76.9; H 8.3; N 4.1%.

EXAMPLES 11 TO 200

By processes similar to these described in Examples 1 to 10 above, further compounds according to the invention were prepared as detailed in Table I below. In this table, the compounds are identified by reference to formula I. Low resolution mass spectroscopy and C,H,N analysis data for the compounds of Examples 11 to 200 are given in Table IA below.

TABLE I

| Ex. No. | R | $R^1$ | $R^2$ | W | X | m | n |
|---|---|---|---|---|---|---|---|
| 11 | —H | phenyl | —H | —$CH_2$— | —$CH_2$— | 0 | 0 |
| 12 | —$CH_2$—CH═$CH_2$ | phenyl | —H | —$CH_2$— | —$CH_2$— | 0 | 0 |
| 13 | phenyl | phenyl | —H | —$CH_2$— | —$CH_2$— | 0 | 2 |
| 14 | —$CH_2CH_2OCH_2CH_3$ | phenyl | —H | —$CH_2$— | —$CH_2$— | 0 | 0 |

TABLE I-continued

| Ex. No. | R | $R^1$ | $R^2$ | W | X | m | n |
|---|---|---|---|---|---|---|---|
| 15 | phenyl | phenyl | —H | $—CH_2—$ | $—CH_2—$ | 0 | 1 |
| 16 | $—(CH_2)_3CH_3$ | phenyl | —H | $—CH_2—$ | $—CH_2—$ | 0 | 0 |
| 17 | $—CH_2C{\equiv}CH$ | phenyl | —H | $—CH_2—$ | $—CH_2—$ | 0 | 0 |
| 18 | $—CH_2CO—OCH_2CH_3$ | phenyl | —H | $—CH_2—$ | $—CH_2—$ | 0 | 0 |
| 19 | tetrahydropyran-2-yloxy | phenyl | —H | $—CH_2—$ | $—CH_2—$ | 0 | 3 |
| 20 | $—(CH_2)_{11}CH_3$ | phenyl | —H | $—CH_2—$ | $—CH_2—$ | 0 | 0 |
| 21 | $—CH_2CH_2CH(CH_3)_2$ | phenyl | —H | $—CH_2—$ | $—CH_2—$ | 0 | 0 |
| 22 | $—CH_2CH(OCH_2CH_3)_2$ | phenyl | —H | $—CH_2—$ | $—CH_2—$ | 0 | 0 |
| 23 | —H | 4-methylphenyl | —H | $—CH_2—$ | $—CH_2—$ | 0 | 0 |
| 24 | $—CH_2CH{=}CH_2$ | 4-methylphenyl | —H | $—CH_2—$ | $—CH_2—$ | 0 | 0 |
| 25 | phenyl | 4-methylphenyl | —H | $—CH_2—$ | $—CH_2—$ | 0 | 2 |
| 26 | $—CH_2CH_2OCH_2CH_3$ | 4-methylphenyl | —H | $—CH_2—$ | $—CH_2—$ | 0 | 0 |
| 27 | cyclohexyl | phenyl | —H | $—CH_2—$ | $—CH_2—$ | 0 | 2 |
| 28 | cyclohexyl | 4-methylphenyl | —H | $—CH_2—$ | $—CH_2—$ | 0 | 2 |
| 29 | tetrahydropyran-2-yloxy | 4-methylphenyl | —H | $—CH_2—$ | $—CH_2—$ | 0 | 3 |
| 30 | phenyl | 4-t-butylphenyl | —H | $—CH_2—$ | $—CH_2—$ | 0 | 1 |
| 31 | phenyl | 4-t-butylphenyl | —H | $—CH_2—$ | $—CH_2—$ | 0 | 2 |
| 32 | cyclohexyl | 4-t-butylphenyl | —H | $—CH_2—$ | $—CH_2—$ | 0 | 2 |
| 33 | $—(CH_2)_{11}CH_3$ | 4-t-butylphenyl | —H | $—CH_2—$ | $—CH_2—$ | 0 | 0 |
| 34 | —H | 4-t-butylphenyl | —H | $—CH_2—$ | $—CH_2—$ | 0 | 0 |
| 35 | $—CH_2CH_2OCH_2CH_3$ | 4-t-butylphenyl | —H | $—CH_2—$ | $—CH_2—$ | 0 | 0 |
| 36 | tetrahydropyran-2-yloxy | 4-t-butylphenyl | —H | $—CH_2—$ | $—CH_2—$ | 0 | 3 |
| 37 | $—CH_2CH(OCH_2CH_3)_2$ | 4-t-butylphenyl | —H | $—CH_2—$ | $—CH_2—$ | 0 | 0 |
| 38 | $—CH_2CH_2CH(CH_3)_2$ | 4-t-butylphenyl | —H | $—CH_2—$ | $—CH_2—$ | 0 | 0 |
| 39 | $—CH_2CH{=}CH_2$ | 4-t-butylphenyl | —H | $—CH_2—$ | $—CH_2—$ | 0 | 0 |
| 40 | $—CH_2C{\equiv}CH$ | 4-t-butylphenyl | —H | $—CH_2—$ | $—CH_2—$ | 0 | 0 |
| 41 | 4-methylphenyl | phenyl | —H | $—CH_2—$ | $—CH_2—$ | 0 | 1 |
| 42 | 4-t-butylphenyl | phenyl | —H | $—CH_2—$ | $—CH_2—$ | 0 | 1 |
| 43 | 3-hydroxyphenyl | 4-t-butylphenyl | —H | $—CH_2—$ | $—CH_2—$ | 0 | 2 |
| 44 | $—CH_2CH_2CH_2CH_2OH$ | 4-t-butylphenyl | —H | $—CH_2—$ | $—CH_2—$ | 0 | 0 |
| 45 | $—CH(CH_3)_2$ | 4-t-butylphenyl | —H | $—CH_2—$ | $—CH_2—$ | 0 | 0 |
| 46 | 4-chlorophenyl | 4-t-butylphenyl | —H | $—CH_2—$ | $—CH_2—$ | 0 | 1 |
| 47 | cyclohexyl | 4-t-butylphenyl | —H | $—CH_2—$ | $—CH_2—$ | 0 | 1 |
| 48 | phenyl | phenyl | —H | $—CH_2—$ | $—CH_2—$ | 0 | 3 |
| 49 | phenyl | 4-t-butylphenyl | —H | $—CH_2—$ | $—CH_2—$ | 0 | 3 |
| 50 | 3-methoxyphenyl | 4-t-butylphenyl | —H | $—CH_2—$ | $—CH_2—$ | 0 | 2 |
| 51 | 3-methoxyphenyl | phenyl | —H | $—CH_2—$ | $—CH_2—$ | 0 | 2 |
| 52 | 4-chlorophenyl | 4-t-butylphenyl | —H | $—CH_2—$ | $—CH_2—$ | 0 | 2 |
| 53 | 4-chlorophenyl | phenyl | —H | $—CH_2—$ | $—CH_2—$ | 0 | 2 |
| 54 | 4-methoxyphenyl | 4-t-butylphenyl | —H | $—CH_2—$ | $—CH_2—$ | 1 | 1 |
| 55 | 4-t-butylphenyl | phenyl | —H | $—CH_2—$ | $—CH_2—$ | 0 | 2 |
| 56 | 4-t-butylphenyl | 4-t-butylphenyl | —H | $—CH_2—$ | $—CH_2—$ | 0 | 2 |
| 57 | 4-methoxyphenyl | 4-t-butylphenyl | —H | $—CH_2—$ | $—CH_2—$ | 0 | 2 |
| 58 | $—(CH_2)_5CH_3$ | 4-t-butylphenyl | —H | $—CH_2—$ | $—CH_2—$ | 0 | 0 |
| 59 | cyclopentyl | phenyl | —H | $—CH_2—$ | $—CH_2—$ | 0 | 2 |
| 60 | cyclopentyl | 4-t-butylphenyl | —H | $—CH_2—$ | $—CH_2—$ | 0 | 2 |
| 61 | naphth-1-yl | phenyl | —H | $—CH_2—$ | $—CH_2—$ | 0 | 2 |
| 62 | naphth-1-yl | 4-t-butylphenyl | —H | $—CH_2—$ | $—CH_2—$ | 0 | 2 |
| 63 | 3-thien-3-yl | 4-t-butylphenyl | —H | $—CH_2—$ | $—CH_2—$ | 0 | 2 |
| 64 | morpholin-4-yl | phenyl | —H | $—CH_2—$ | $—CH_2—$ | 0 | 2 |
| 65 | cyclohexyl | phenyl | —H | $—CH_2—$ | $—CH_2—$ | 0 | 1 |
| 66 | cyclohexyl | 4-methylphenyl | —H | $—CH_2—$ | $—CH_2—$ | 0 | 1 |
| 67 (HCl salt) | phenyl | 4-t-butylphenyl | —H | $—CH_2—$ | $—CH_2—$ | 0 | 1 |
| 68 (saccharin salt) | phenyl | 4-t-butylphenyl | —H | $—CH_2—$ | $—CH_2—$ | 0 | 1 |
| 69 | 4-chlorophenyl | phenyl | —H | $—CH_2—$ | $—CH_2—$ | 0 | 1 |
| 70 | 4-bromophenyl | phenyl | —H | $—CH_2—$ | $—CH_2—$ | 0 | 1 |
| 71 | 4-bromophenyl | 4-t-butylphenyl | —H | $—CH_2—$ | $—CH_2—$ | 0 | 1 |
| 72 | 4-fluorophenyl | phenyl | —H | $—CH_2—$ | $—CH_2—$ | 0 | 1 |
| 73 | 4-fluorophenyl | 4-t-butylphenyl | —H | $—CH_2—$ | $—CH_2—$ | 0 | 1 |
| 74 | —H | 4-isopropylphenyl | —H | $—CH_2—$ | $—CH_2—$ | 0 | 0 |
| 75 | phenyl | 4-isopropylphenyl | —H | $—CH_2—$ | $—CH_2—$ | 0 | 1 |
| 76 | phenyl | 4-isopropylphenyl | —H | $—CH_2—$ | $—CH_2—$ | 0 | 2 |
| 77 | 3-pyridyl | phenyl | —H | $—CH_2—$ | $—CH_2—$ | 0 | 1 |
| 78 | 3-pyridyl | 4-t-butylphenyl | —H | $—CH_2—$ | $—CH_2—$ | 0 | 1 |
| 79 | 3-methoxyphenyl | phenyl | —H | $—CH_2—$ | $—CH_2—$ | 0 | 1 |
| 80 | 3-methoxyphenyl | 4-t-butylphenyl | —H | $—CH_2—$ | $—CH_2—$ | 0 | 1 |
| 81 | imidazol-1-yl | phenyl | —H | $—CH_2—$ | $—CH_2—$ | 1 | 0 |
| 82 | 3-chlorophenyl | phenyl | —H | $—CH_2—$ | $—CH_2—$ | 0 | 1 |
| 83 | 3-chlorophenyl | 4-t-butylphenyl | —H | $—CH_2—$ | $—CH_2—$ | 0 | 1 |
| 84 | —H | phenyl | $—CH_3$ | $—CH_2—$ | $—CH_2—$ | 0 | 0 |
| 85 | 2,4-dichlorophenyl | 4-t-butylphenyl | —H | $—CH_2—$ | $—CH_2—$ | 0 | 1 |
| 86 | cyclohexyl | 4-isopropylphenyl | —H | $—CH_2—$ | $—CH_2—$ | 0 | 2 |
| 87 | 4-chlorophenyl | 4-isopropylphenyl | —H | $—CH_2—$ | $—CH_2—$ | 0 | 1 |
| 88 | 4-nitrophenyl | 4-t-butylphenyl | —H | $—CH_2—$ | $—CH_2—$ | 0 | 1 |
| 89 | 4-chlorophenyl | phenyl | $—CH_3$ | $—CH_2—$ | $—CH_2—$ | 0 | 1 |
| 90 | phenyl | phenyl | $—CH_3$ | $—CH_2—$ | $—CH_2—$ | 0 | 1 |
| 91 | phenyl | phenyl | $—CH_3$ | $—CH_2—$ | $—CH_2—$ | 0 | 2 |
| 92 | 2-chlorophenyl | phenyl | —H | $—CH_2—$ | $—CH_2—$ | 0 | 1 |
| 93 | 4-cyanophenyl | phenyl | —H | $—CH_2—$ | $—CH_2—$ | 0 | 1 |

TABLE I-continued

| Ex. No. | R | $R^1$ | $R^2$ | W | X | m | n |
|---|---|---|---|---|---|---|---|
| 94 | $-CH_2CH_2CH(CH_3)_2$ | 4-isopropylphenyl | —H | $-CH_2-$ | $-CH_2-$ | 0 | 0 |
| 95 | —H | 4-chlorophenyl | —H | $-CH_2-$ | $-CH_2-$ | 0 | 0 |
| 96 | 4-chlorophenyl | 4-chlorophenyl | —H | $-CH_2-$ | $-CH_2-$ | 0 | 1 |
| 97 | cyclohexyl | 4-chlorophenyl | —H | $-CH_2-$ | $-CH_2-$ | 0 | 1 |
| 98 | $-CH_2CH_2CH(CH_3)_2$ | 4-chlorophenyl | —H | $-CH_2-$ | $-CH_2-$ | 0 | 0 |
| 99 | cyclohexyl | 4-chlorophenyl | —H | $-CH_2-$ | $-CH_2-$ | 0 | 2 |
| 100 | cyclohexyl | 4-isopropylphenyl | —H | $-CH_2-$ | $-CH_2-$ | 0 | 1 |
| 101 | phenyl | 4-chlorophenyl | —H | $-CH_2-$ | $-CH_2-$ | 0 | 1 |
| 102 | phenyl | 4-chlorophenyl | —H | $-CH_2-$ | $-CH_2-$ | 0 | 2 |
| 103 | tetrahydropyran-2-yl | phenyl | —H | $-CH_2-$ | $-CH_2-$ | 0 | 1 |
| 104 | phenyl | 4-methoxyphenyl | —H | $-CH_2-$ | $-CH_2-$ | 0 | 1 |
| 105 | phenyl | 4-methoxyphenyl | —H | $-CH_2-$ | $-CH_2-$ | 0 | 2 |
| 106 | cyclohexyl | 4-methoxyphenyl | —H | $-CH_2-$ | $-CH_2-$ | 0 | 1 |
| 107 | cyclohexyl | 4-methoxyphenyl | —H | $-CH_2-$ | $-CH_2-$ | 0 | 2 |
| 108 | $-CH_2CH_2CH(CH_3)_2$ | 4-methoxyphenyl | —H | $-CH_2-$ | $-CH_2-$ | 0 | 0 |
| 109 | —H | 4-methoxyphenyl | —H | $-CH_2-$ | $-CH_2-$ | 0 | 0 |
| 110 | 4-chlorophenyl | 4-methoxyphenyl | —H | $-CH_2-$ | $-CH_2-$ | 0 | 1 |
| 111 | $-(CH_2)_5CH_3$ | 4-chlorophenyl | —H | $-CH_2-$ | $-CH_2-$ | 0 | 0 |
| 112 | $-(CH_2)_5CH_3$ | phenyl | —H | $-CH_2-$ | $-CH_2-$ | 0 | 0 |
| 113 | $-(CH_2)_4CH_3$ | 4-t-butylphenyl | —H | $-CH_2-$ | $-CH_2-$ | 0 | 0 |
| 114 | 1-hydroxynaphth-2-yl | phenyl | —H | $-CH_2-$ | $-CH_2-$ | 0 | 1 |
| 115 | 4-chlorophenylcarbonyl | phenyl | —H | $-CH_2-$ | $-CH_2-$ | 0 | 1 |
| 116 | $-(CH_2)_5CH_3$ | 4-methoxyphenyl | —H | $-CH_2-$ | $-CH_2-$ | 0 | 0 |
| 117 | $-(CH_2)_5CH_3$ | 4-isopropylphenyl | —H | $-CH_2-$ | $-CH_2-$ | 0 | 0 |
| 118 | —H | cyclohexyl | —H | $-CH_2-$ | $-CH_2-$ | 0 | 0 |
| 119 | phenyl | cyclohexyl | —H | $-CH_2-$ | $-CH_2-$ | 0 | 1 |
| 120 | cyclohexyl | cyclohexyl | —H | $-CH_2-$ | $-CH_2-$ | 0 | 1 |
| 121 | cyclohexyl | cyclohexyl | —H | $-CH_2-$ | $-CH_2-$ | 0 | 2 |
| 122 | 4-chlorophenyl | cyclohexyl | —H | $-CH_2-$ | $-CH_2-$ | 0 | 1 |
| 123 | phenyl | cyclohexyl | —H | $-CH_2-$ | $-CH_2-$ | 0 | 2 |
| 124 | $-(CH_2)_5CH_3$ | cyclohexyl | —H | $-CH_2-$ | $-CH_2-$ | 0 | 0 |
| 125 | phenyl | 4-chlorophenyl | —H | $-CH_2-$ | —O— | 0 | 1 |
| 126 | 4-chlorophenyl | phenyl | —H | $-CH_2-$ | —O— | 0 | 1 |
| 127 | phenyl | phenyl | —H | $-CH_2-$ | —O— | 0 | 2 |
| 128 | $-CH{=}CH_2$ | phenyl | —H | $-CH_2-$ | $-CH_2-$ | 0 | 1 |
| 129 | $-CH_3$ | phenyl | —H | $-CH_2-$ | $-CH_2-$ | 0 | 3 |
| 130 | $-C{\equiv}CH$ | phenyl | —H | $-CH_2-$ | $-CH_2-$ | 0 | 1 |
| 131 | $-(CH_2)_8CH_3$ | phenyl | —H | $-CH_2-$ | $-CH_2-$ | 0 | 3 |
| 132 | $-CH_2CH(CH_3)_2$ | phenyl | —H | $-CH_2-$ | $-CH_2-$ | 0 | 1 |
| 133 | $-(CH_2)_9CH_3$ | 4-t-butylphenyl | —H | $-CH_2-$ | $-CH_2-$ | 0 | 2 |
| 134 | $-CH_2OH$ | 4-t-butylphenyl | —H | $-CH_2-$ | $-CH_2-$ | 0 | 3 |
| 135 | $-CH_2CH_3$ | 4-t-butylphenyl | —H | $-CH_2-$ | $-CH_2-$ | 0 | 3 |
| 136 | cyclohexyl | phenyl | —H | $-CH_2-$ | —O— | 0 | 1 |
| 137 | $-(CH_2)_5CH_3$ | phenyl | —H | $-CH_2-$ | —O— | 0 | 0 |
| 138 | phenyl | 4-fluorobenzyl | —H | $-CH_2-$ | —O— | 0 | 1 |
| 139 | cyclohexyl | phenyl | —H | $-CH_2-$ | —O— | 0 | 2 |
| 140 | $-(CH_2)_4CH_3$ | phenyl | —H | $-CH_2-$ | $-CH_2-$ | 0 | 0 |
| 141 | $-(CH_2)_6CH_3$ | phenyl | —H | $-CH_2-$ | $-CH_2-$ | 0 | 0 |
| 142 | $-(CH_2)_7CH_3$ | 4-t-butylphenyl | —H | $-CH_2-$ | $-CH_2-$ | 0 | 0 |
| 143 | 4-biphenylyl | phenyl | —H | $-CH_2-$ | $-CH_2-$ | 0 | 1 |
| 144 | $-OCH_2CH_2OCH_3$ | phenyl | —H | $-CH_2-$ | $-CH_2-$ | 0 | 2 |
| 145 | $-OCH_2CH_2OCH_3$ | 4-t-butylphenyl | —H | $-CH_2-$ | $-CH_2-$ | 0 | 2 |
| 146 | 2-pyridyl | phenyl | —H | $-CH_2-$ | $-CH_2-$ | 0 | 1 |
| 147 | 4-pyridyl | phenyl | —H | $-CH_2-$ | $-CH_2-$ | 0 | 1 |
| 148 | $-(CH_2)_6CH_3$ | 4-t-butylphenyl | —H | $-CH_2-$ | $-CH_2-$ | 0 | 0 |
| 149 | 2-pyridyl | 4-t-butylphenyl | —H | $-CH_2-$ | $-CH_2-$ | 0 | 1 |
| 150 | 4-pyridyl | 4-t-butylphenyl | —H | $-CH_2-$ | $-CH_2-$ | 0 | 1 |
| 151 | 4-biphenylyl | 4-t-butylphenyl | —H | $-CH_2-$ | $-CH_2-$ | 0 | 1 |
| 152 | cyclopentyl | 4-t-butylphenyl | —H | $-CH_2-$ | $-CH_2-$ | 0 | 1 |
| 153 | 2-tetrahydrofuryl | 4-t-butylphenyl | —H | $-CH_2-$ | $-CH_2-$ | 0 | 1 |
| 154 | cyclopentyl | phenyl | —H | $-CH_2-$ | $-CH_2-$ | 0 | 1 |
| 155 | 2-tetrahydrofuryl | phenyl | —H | $-CH_2-$ | $-CH_2-$ | 0 | 1 |
| 156 | 2-furyl | phenyl | —H | $-CH_2-$ | $-CH_2-$ | 1 | 0 |
| 157 | 2-furyl | 4-t-butylphenyl | —H | $-CH_2-$ | $-CH_2-$ | 1 | 0 |
| 158 | 2-furyl | phenyl | —H | $-CH_2-$ | $-CH_2-$ | 0 | 1 |
| 159 | 2-furyl | 4-t-butylphenyl | —H | $-CH_2-$ | $-CH_2-$ | 0 | 1 |
| 160 (saccharin salt) | 4-bromophenyl | phenyl | —H | $-CH_2-$ | $-CH_2-$ | 0 | 1 |
| 161 (saccharin salt) | 4-bromophenyl | 4-t-butylphenyl | —H | $-CH_2-$ | $-CH_2-$ | 0 | 1 |
| 162 | $-OC(CH_3)_3$ | phenyl | —H | $-CH_2-$ | $-CH_2-$ | 1 | 0 |
| 163 (saccharin salt) | 4-fluorophenyl | 4-t-butylphenyl | —H | $-CH_2-$ | $-CH_2-$ | 0 | 1 |
| 164 (saccharin salt) | phenyl | phenyl | —H | $-CH_2-$ | $-CH_2-$ | 0 | 3 |
| 165 | 2-methylphenyl | 4-t-butylphenyl | —H | $-CH_2-$ | $-CH_2-$ | 0 | 1 |
| 166 | 3-(2,4-dichlorophen-oxy)2-hydroxypropyl | 4-t-butylphenyl | —H | $-CH_2-$ | $-CH_2-$ | 0 | 0 |
| 167 | 3-(2,4-dichlorophen-oxy)-2-hydroxypropyl | phenyl | —H | $-CH_2-$ | $-CH_2-$ | 0 | 0 |
| 168 | —H | phenyl | —H | $-CH_2CH_2-$ | $-CH_2-$ | 0 | 0 |

TABLE I-continued

| Ex. No. | R | $R^1$ | $R^2$ | W | X | m | n |
|---|---|---|---|---|---|---|---|
| 169 | 4-chlorophenyl | phenyl | —H | $-CH_2CH_2-$ | $-CH_2-$ | 0 | 2 |
| 170 | —H | phenyl | —H | $-CH_2-$ | $-CH_2CH_2-$ | 0 | 0 |
| 171 | phenyl | phenyl | —H | $-CH_2-$ | $-CH_2CH_2-$ | 0 | 2 |
| 172 | cyclohexyl | phenyl | —H | $-CH_2-$ | $-CH_2CH_2-$ | 0 | 2 |
| 173 | 4-chlorophenyl | phenyl | —H | $-CH_2-$ | $-CH_2CH_2-$ | 0 | 1 |
| 174 | cyclohexyl | phenyl | —H | $-CH_2-$ | $-CH_2CH_2-$ | 0 | 1 |
| 175 | $-(CH_2)_5CH_3$ | phenyl | —H | $-CH_2-$ | $-CH_2CH-$ | 0 | 0 |
| 176 | phenyl | 4-t-butylphenyl | —H | —O— | $-CH_2-$ | 0 | 1 |
| 177 | phenyl | phenyl | —H | —O— | $-CH_2-$ | 0 | 1 |
| 178 | 4-chlorophenyl | 4-t-butylphenyl | —H | —O— | $-CH_2-$ | 0 | 1 |
| 179 | phenyl | 4-t-butylphenyl | —H | —O— | $-CH_2-$ | 0 | 2 |
| 180 (HCl salt) | —H | 4-t-butylphenyl | —H | —O— | $-CH_2-$ | 0 | 0 |
| 181 | 4-chlorophenyl | 4-t-butylphenyl | —H | —O— | $-CH_2-$ | 0 | 2 |
| 182 | 4-chlorophenyl | phenyl | —H | —O— | $-CH_2-$ | 0 | 2 |
| 183 | 4-chlorophenyl | phenyl | —H | —O— | $-CH_2-$ | 0 | 1 |
| 184 | 4-bromophenyl | phenyl | —H | —O— | $-CH_2-$ | 0 | 1 |
| 185 | naphth-1-yl | phenyl | —H | $-CH_2-$ | $-CH_2-$ | 0 | 1 |
| 186 | naphth-1-yl | 4-t-butylphenyl | —H | $-CH_2-$ | $-CH_2-$ | 0 | 1 |
| 187 | cyclohexyl | phenyl | —H | $-CH_2-$ | $-CH_2-$ | 0 | 0 |
| 188 | 4-nitrophenyl | phenyl | —H | $-CH_2-$ | $-CH_2-$ | 0 | 0 |
| 189 | 4-aminophenyl | phenyl | —H | $-CH_2-$ | $-CH_2-$ | 0 | 0 |
| 190 | cyclohexyl | 4-t-butylphenyl | —H | $-CH_2-$ | $-CH_2-$ | 0 | 0 |
| 191 | phenyl | phenyl | —H | $-CH_2-$ | $-CH_2-$ | 0 | 0 |
| 192 | phenyl | phenyl | —H | $-CH_2-$ | single bond | 0 | 1 |
| 193 | phenyl | phenyl | —H | $-CH_2-$ | single bond | 0 | 2 |
| 194 | 4-chlorophenyl | phenyl | —H | $-CH_2-$ | single bond | 0 | 1 |
| 195 | $-(CH_2)_5CH_3$ | phenyl | —H | $-CH_2-$ | single bond | 0 | 0 |
| 196 | phenyl | 4-t-butylphenyl | —H | $-CH_2-$ | single bond | 0 | 1 |
| 197 | phenyl | 4-t-butylphenyl | —H | $-CH_2-$ | single bond | 0 | 2 |
| 198 | 4-chlorophenyl | 4-t-butylphenyl | —H | $-CH_2-$ | single bond | 0 | 1 |
| 199 | $-(CH_2)_5CH_3$ | 4-t-butylphenyl | —H | $-CH_2-$ | single bond | 0 | 0 |
| 200 | $-(CH_2)_2CH_3$ | 4-t-butylphenyl | —H | $-CH_2-$ | single bond | 0 | 3 |

TABLE IA

| Example No. | | $M^+$ Found | Analysis % C Calc. | C Found | H Calc. | H Found | N Calc. | N Found |
|---|---|---|---|---|---|---|---|---|
| | b.pt °C. (mmHg) | | | | | | | |
| 11 | 110 (0.05) | 175 | 82.2 | 80.9 | 9.8 | 9.9 | 8.0 | 8.3 |
| 12 | | 215 | 83.7 | 83.9 | 9.8 | 9.8 | 6.5 | 7.5 |
| 13 | | 279 | 86.0 | 85.6 | 9.0 | 9.0 | 5.0 | 5.2 |
| 14 | | 247 | 77.7 | 77.8 | 10.2 | 10.3 | 5.7 | 5.9 |
| 15 | | 265 | 86.0 | 86.7 | 8.7 | 8.9 | 5.3 | 6.2 |
| 16 | | 231 | 83.1 | 83.3 | 10.9 | 10.8 | 6.1 | 6.0 |
| 17 | | 213 | 84.5 | 84.7 | 9.0 | 9.2 | 6.6 | 6.8 |
| 18 | | 261 | 73.5 | 73.4 | 8.9 | 9.1 | 5.4 | 5.6 |
| 19 | | 317 | 75.7 | 75.8 | 9.8 | 9.9 | 4.4 | 4.7 |
| 20 | | 343 | 83.9 | 83.4 | 12.0 | 12.0 | 4.1 | 4.3 |
| 21 | | 245 | 83.2 | 83.1 | 11.1 | 11.0 | 5.7 | 6.1 |
| 22 | | 291 | 74.2 | 73.9 | 10.0 | 10.2 | 4.8 | 5.1 |
| 23 | 114–117 (0.5) | 189 | 82.5 | 82.1 | 10.1 | 10.4 | 7.4 | 7.6 |
| 24 | | 229 | 83.8 | 83.5 | 10.1 | 10.3 | 6.1 | 6.3 |
| 25 | | 293 | 86.0 | 86.4 | 9.3 | 9.4 | 4.8 | 5.0 |
| 26 | | 261 | 78.1 | 78.4 | 10.4 | 10.5 | 5.4 | 5.8 |
| 27 | | 285 | 84.2 | 83.7 | 10.9 | 11.1 | 4.9 | 5.2 |
| 28 | | 299 | 84.2 | 83.4 | 11.1 | 11.1 | 4.7 | 5.1 |
| 29 | | 331 | 76.1 | 76.1 | 10.0 | 10.0 | 4.2 | 4.5 |
| 30 | | 321 | 85.9 | 85.9 | 9.7 | 10.0 | 4.4 | 4.6 |
| 31 | | 335 | 85.9 | 85.5 | 9.9 | 10.1 | 4.2 | 4.5 |
| 32 | | 341 | 84.4 | 84.2 | 11.5 | 11.5 | 4.1 | 4.4 |
| 33 | | 399 | 84.1 | 84.5 | 12.4 | 12.6 | 3.5 | 4.4 |
| 34 | 114–120 (0.1) | 231 | 83.1 | 82.7 | 10.9 | 11.1 | 6.1 | 5.9 |
| 35 | | 303 | 79.2 | 79.2 | 11.0 | 11.5 | 4.6 | 4.6 |
| 36 | | 373 | 77.2 | 76.8 | 10.5 | 10.6 | 3.7 | 4.1 |
| 37 | | 347 | 76.0 | 74.7 | 10.7 | 10.8 | 4.0 | 4.3 |
| 38 | | 301 | 83.7 | 83.8 | 11.7 | 11.9 | 4.6 | 4.8 |
| 39 | | 271 | 84.1 | 84.1 | 10.8 | 10.7 | 5.2 | 5.6 |
| 40 | | 269 | 84.7 | 84.7 | 10.1 | 9.9 | 5.2 | 5.9 |
| | m.pt °C. | | | | | | | |
| 41 | | 279 | 86.0 | 85.9 | 9.0 | 9.3 | 5.0 | 5.3 |
| 42 | | 321 | 85.9 | 85.0 | 9.7 | 9.8 | 4.4 | 4.6 |
| 43 | | 351 | 82.0 | 80.3 | 9.5 | 9.3 | 4.0 | 3.9 |
| 44 | | 303 | 79.2 | 73.3 | 11.0 | 10.7 | 4.6 | 4.0 |
| 45 | | 273 | 83.5 | 83.1 | 11.4 | 11.1 | 5.1 | 5.1 |

TABLE IA-continued

| Example No. | | M+ Found | Analysis % C Calc. | C Found | H Calc. | H Found | N Calc. | N Found |
|---|---|---|---|---|---|---|---|---|
| 46 | | 355/357 | 77.6 | 77.0 | 8.5 | 8.6 | 3.9 | 4.1 |
| 47 | | 327 | 84.3 | 83.3 | 11.4 | 11.0 | 4.3 | 4.8 |
| 48 | | 293 | 86.0 | 85.8 | 9.3 | 9.3 | 4.8 | 5.0 |
| 49 | | 349 | 85.9 | 85.6 | 10.1 | 10.2 | 4.0 | 4.3 |
| 50 | | 365 | 82.1 | 82.0 | 9.7 | 9.6 | 3.8 | 4.1 |
| 51 | | 309 | 81.5 | 81.6 | 8.8 | 8.8 | 4.5 | 4.8 |
| 52 | | 369/371 | 77.9 | 77.9 | 8.7 | 8.5 | 3.8 | 4.1 |
| 53 | | 313/315 | 76.5 | 76.8 | 7.7 | 7.8 | 4.5 | 4.9 |
| 54 | | 379 | 79.1 | 79.1 | 8.8 | 8.9 | 3.7 | 3.8 |
| 55 | | 335 | 85.9 | 86.1 | 9.9 | 9.7 | 4.2 | 4.3 |
| 56 | | 391 | 85.9 | 85.6 | 10.6 | 10.6 | 3.6 | 3.6 |
| 57 | | 365 | 82.1 | 81.6 | 9.7 | 9.6 | 3.8 | 4.0 |
| 58 | | 315 | 83.7 | 84.8 | 11.8 | 11.8 | 4.4 | 4.9 |
| 59 | | 271 | 84.1 | 83.9 | 10.8 | 10.9 | 5.2 | 5.2 |
| 60 | | 327 | 83.4 | 81.9 | 11.4 | 11.3 | 4.3 | 4.1 |
| 61 | | 329 | 87.5 | 87.3 | 8.3 | 8.5 | 4.3 | 4.4 |
| 62 | | 385 | 87.2 | 86.0 | 9.0 | 9.2 | 3.6 | 3.6 |
| 63 | | 341 | 77.4 | 77.6 | 9.1 | 9.2 | 4.1 | 4.1 |
| 64 | | 288 | 75.0 | 74.8 | 9.8 | 9.8 | 9.7 | 9.8 |
| 65 | | 271 | 84.1 | 83.7 | 10.8 | 10.5 | 5.2 | 5.6 |
| 66 | | 285 | 84.2 | 79.7 | 10.9 | 10.3 | 4.9 | 5.4 |
| 67 | 208-210 | 321 (M+-HCl) | 73.5 | 72.8 | 9.1 | 8.8 | 3.7 | 3.7 |
| 68 | | 321 (M+-Saccharin) | 71.4 | 70.6 | 7.2 | 7.8 | 5.6 | 5.4 |
| 69 | | 299/301 | 76.1 | 76.1 | 7.4 | 7.7 | 4.7 | 5.3 |
| | b.pt °C. (mmHg) | | | | | | | |
| 70 | | 343/345 | 66.3 | 66.1 | 6.4 | 6.4 | 4.1 | 4.1 |
| 71 | | 399/401 | 69.0 | 69.1 | 7.6 | 7.6 | 3.5 | 3.4 |
| 72 | | 283 | 80.5 | 80.7 | 7.8 | 7.9 | 4.9 | 5.0 |
| 73 | | 339 | 81.4 | 81.1 | 8.9 | 9.0 | 4.1 | 4.4 |
| 74 | 122-124 (1.5) | 217 | 82.9 | 82.7 | 10.6 | 11.0 | 6.4 | 5.8 |
| 75 | | 307 | 85.9 | 85.6 | 9.5 | 9.6 | 4.6 | 4.1 |
| 76 | | 321 | 85.9 | 85.6 | 9.7 | 9.8 | 4.4 | 4.2 |
| 77 | | 266 | 81.2 | 80.8 | 8.3 | 8.4 | 10.5 | 9.9 |
| 78 | | 322 | 81.9 | 80.7 | 9.4 | 9.3 | 8.7 | 8.3 |
| 79 | | 295 | 81.3 | 80.7 | 8.5 | 8.5 | 4.7 | 4.6 |
| 80 | | 351 | 82.0 | 79.9 | 9.5 | 9.3 | 4.0 | 4.1 |
| 81 | | 269 | 71.4 | 71.3 | 7.1 | 7.4 | 15.6 | 13.6 |
| 82 | | 299/301 | 76.1 | 76.3 | 7.4 | 7.5 | 4.7 | 4.5 |
| 83 | | 355/357 | 77.6 | 76.7 | 8.5 | 8.5 | 3.9 | 3.4 |
| 84 | | 189 | 82.5 | 80.4 | 10.1 | 10.2 | 7.4 | 7.4 |
| 85 | | 389 | 70.7 | 70.3 | 7.5 | 7.6 | 3.6 | 3.4 |
| | m.pt °C. | | | | | | | |
| 86 | | 327 | 84.3 | 84.8 | 11.4 | 11.6 | 4.3 | 4.3 |
| 87 | | 341/343 | 77.3 | 76.7 | 8.3 | 8.1 | 4.1 | 3.7 |
| 88 | | 366 | 75.4 | 75.4 | 8.3 | 8.3 | 7.6 | 7.6 |
| 89 | | 313/315 | 76.5 | 74.9 | 7.7 | 7.6 | 4.5 | 4.7 |
| 90 | | 279 | 86.0 | 85.8 | 9.0 | 9.2 | 5.0 | 5.1 |
| 91 | | 293 | 86.0 | 85.9 | 9.3 | 9.3 | 4.8 | 4.8 |
| 92 | | 299/301 | 76.1 | 76.5 | 7.4 | 7.5 | 4.7 | 4.3 |
| 93 | | 290 | 82.7 | 82.8 | 7.6 | 7.7 | 9.6 | 9.8 |
| 94 | | 287 | 83.6 | 81.8 | 11.6 | 11.5 | 4.9 | 4.7 |
| 95 | | 209 | 68.7 | 65.7 | 7.7 | 7.6 | 6.7 | 5.6 |
| 96 | | 333 | 68.3 | 67.7 | 6.3 | 6.4 | 4.2 | 4.2 |
| 97 | | 305/307 | 74.6 | 75.0 | 9.2 | 9.3 | 4.6 | 4.6 |
| 98 | | 279/281 | 73.0 | 72.4 | 9.4 | 9.5 | 5.0 | 4.9 |
| 99 | | 319/321 | 75.1 | 75.4 | 9.5 | 9.7 | 4.4 | 4.1 |
| 100 | | 313 | 84.3 | 85.3 | 11.3 | 11.6 | 4.5 | 4.6 |
| 101 | | 299/301 | 76.1 | 76.1 | 7.4 | 7.5 | 4.7 | 5.0 |
| 102 | | 313/315 | 76.5 | 76.4 | 7.7 | 7.9 | 4.5 | 4.6 |
| 103 | | 273 | 79.1 | 77.4 | 10.0 | 9.8 | 5.1 | 5.3 |
| 104 | | 295 | 81.3 | 81.8 | 8.5 | 8.7 | 4.7 | 4.2 |
| 105 | | 309 | 81.5 | 81.7 | 8.8 | 9.1 | 4.5 | 4.0 |
| 106 | | 301 | 79.7 | 80.7 | 10.4 | 10.3 | 4.6 | 4.8 |
| 107 | | 315 | 80.0 | 80.7 | 10.5 | 10.9 | 4.4 | 4.7 |
| 108 | | 275 | 78.5 | 79.7 | 10.6 | 10.9 | 5.1 | 5.3 |
| 109 | | 205 | 76.1 | 73.2 | 9.3 | 9.3 | 6.8 | 5.6 |
| 110 | | 329/331 | 72.8 | 73.1 | 7.3 | 7.5 | 4.2 | 4.3 |
| 111 | | 293/295 | 73.6 | 73.8 | 9.6 | 9.9 | 4.8 | 4.6 |
| 112 | | 259 | 83.3 | 84.5 | 11.3 | 11.7 | 5.4 | 5.6 |
| 113 | | 301 | 83.7 | 83.9 | 11.7 | 11.5 | 4.6 | 4.6 |
| 114 | | 331 | 83.3 | 83.4 | 7.6 | 7.7 | 4.2 | 4.2 |
| 115 | | 327/329 | 73.3 | 70.6 | 6.8 | 6.5 | 4.3 | 4.3 |
| 116 | | 289 | 78.8 | 78.7 | 10.8 | 10.8 | 4.8 | 4.6 |
| 117 | | 301 | 83.7 | 83.9 | 11.7 | 11.8 | 4.6 | 5.0 |

TABLE IA-continued

| Example No. | | M+ Found | Analysis % C Calc. | C Found | H Calc. | H Found | N Calc. | N Found |
|---|---|---|---|---|---|---|---|---|
| 118 | | 181 | 79.5 | 78.3 | 12.8 | 12.8 | 7.7 | 7.6 |
| 119 | | 271 | 84.1 | 83.7 | 10.8 | 10.6 | 5.2 | 5.2 |
| 120 | | 277 | 82.2 | 83.1 | 12.7 | 12.8 | 5.0 | 5.0 |
| 121 | | 291 | 82.4 | 80.4 | 12.8 | 12.9 | 4.8 | 5.0 |
| 122 | | 305/307 | 74.6 | 74.8 | 9.2 | 9.4 | 4.6 | 4.7 |
| 123 | | 285 | 84.1 | 83.0 | 10.9 | 10.7 | 4.9 | 5.9 |
| 124 | | 265 | 81.4 | 80.8 | 13.3 | 13.2 | 5.3 | 6.0 |
| 125 | | 301/303 | 71.6 | 72.2 | 6.7 | 7.1 | 4.6 | 4.3 |
| 126 | | 301/303 | 71.6 | 71.4 | 6.7 | 6.6 | 4.6 | 5.3 |
| 127 | | 281 | 81.1 | 81.5 | 8.2 | 8.3 | 4.9 | 5.5 |
| 128 | | 215 | 83.7 | 83.9 | 9.8 | 9.8 | 6.5 | 7.5 |
| 129 | | 231 | 83.1 | 83.3 | 10.9 | 10.8 | 6.1 | 6.0 |
| 130 | | 213 | 84.5 | 84.7 | 9.0 | 9.2 | 6.6 | 6.8 |
| 131 | | 343 | 83.9 | 83.4 | 12.0 | 12.0 | 4.1 | 4.3 |
| 132 | | 245 | 83.2 | 83.1 | 11.1 | 11.0 | 5.7 | 6.1 |
| 133 | | 399 | 84.1 | 84.5 | 12.4 | 12.6 | 3.5 | 4.4 |
| 134 | | 303 | 79.2 | 73.3 | 11.0 | 10.7 | 4.6 | 4.0 |
| 135 | | 301 | 83.7 | 83.9 | 11.7 | 11.5 | 4.6 | 4.6 |
| 136 | | 273 | 78.1 | 78.9 | 9.9 | 10.2 | 5.1 | 5.1 |
| 137 | | 261 | 78.1 | 77.2 | 10.4 | 10.4 | 5.4 | 5.6 |
| 138 | | 299 | 76.2 | 76.3 | 7.4 | 7.5 | 4.6 | 4.7 |
| 139 | | 287 | 79.4 | 80.2 | 10.2 | 10.3 | 4.9 | 5.4 |
| 140 | | 245 | 83.2 | 82.1 | 11.1 | 11.1 | 5.7 | 6.2 |
| 141 | | 273 | 83.5 | 82.5 | 11.4 | 11.1 | 5.1 | 5.4 |
| 142 | | 343 | 83.9 | 82.6 | 12.0 | 12.0 | 4.1 | 4.2 |
| 143 | | 341 | 87.9 | 87.8 | 8.0 | 8.1 | 4.1 | 4.0 |
| 144 | | 277 | 73.6 | 73.6 | 9.8 | 9.8 | 5.1 | 5.5 |
| 145 | | 333 | 75.7 | 75.8 | 10.6 | 10.3 | 4.2 | 4.7 |
| 146 | | 266 | 81.2 | 80.8 | 8.3 | 8.4 | 10.5 | 10.0 |
| 147 | | 266 | 81.2 | 81.1 | 8.3 | 8.5 | 10.5 | 10.6 |
| 148 | | 329 | 83.8 | 83.7 | 11.9 | 12.3 | 4.3 | 4.9 |
| 149 | | 322 | 81.9 | 80.4 | 9.4 | 9.6 | 8.7 | 8.1 |
| 150 | | 322 | 81.9 | 77.4 | 9.4 | 8.4 | 8.7 | 8.5 |
| 151 | | 397 | 87.6 | 87.1 | 8.9 | 9.0 | 3.5 | 3.9 |
| 152 | | 313 | 84.3 | 84.8 | 11.3 | 11.7 | 4.5 | 3.9 |
| 153 | | 315 | 79.9 | 80.3 | 10.5 | 10.1 | 5.1 | 4.8 |
| 154 | | 257 | 79.3 | 84.1 | 10.6 | 11.0 | 5.4 | 5.4 |
| 155 | | 259 | 78.7 | 77.4 | 9.7 | 9.6 | 5.4 | 5.7 |
| 156 | | 269 | 75.8 | 75.7 | 7.1 | 7.2 | 5.2 | 5.5 |
| 157 | | 269 | 77.5 | 77.5 | 8.4 | 8.2 | 4.3 | 5.4 |
| 158 | | 255 | 80.8 | 81.5 | 8.3 | 8.3 | 5.5 | 6.5 |
| 159 | | 311 | 80.9 | 81.6 | 9.4 | 9.4 | 4.5 | 5.0 |
| 160 | | 344 (M+-Saccharin) | 59.2 | 60.1 | 5.2 | 5.5 | 5.3 | 5.3 |
| 161 | | 400 (M+-Saccharin) | 61.7 | 61.9 | 6.1 | 6.2 | 4.8 | 5.8 |
| 162 | | 275 | 74.2 | 74.0 | 9.2 | 9.2 | 5.1 | 5.1 |
| 163 | | 339 (M+-Saccharin) | 68.9 | 65.8 | 6.8 | 6.3 | 5.4 | 5.9 |
| 164 | | 293 (M+-Saccharin) | 70.6 | 69.5 | 6.8 | 6.8 | 5.9 | 6.1 |
| 165 | | 335 | 85.9 | 86.5 | 9.9 | 9.8 | 4.2 | 4.3 |
| 166 | | 450 | 66.7 | 65.7 | 7.4 | 7.3 | 3.1 | 3.3 |
| 167 | | 393 | 64.0 | 63.8 | 6.4 | 6.4 | 3.6 | 3.9 |
| 168 | | 189 | 82.5 | 81.4 | 10.1 | 10.4 | 7.4 | 6.8 |
| 169 | | 327/329 | 76.9 | 76.9 | 8.0 | 8.0 | 4.3 | 4.5 |
| 170 | | 189 | 82.5 | 81.1 | 10.0 | 10.0 | 7.4 | 7.9 |
| 171 | | 293 | 86.0 | 85.9 | 9.3 | 9.5 | 4.8 | 5.1 |
| 172 | | 299 | 84.2 | 85.2 | 11.1 | 11.4 | 4.7 | 5.1 |
| 173 | | 313/315 | 76.5 | 77.5 | 7.7 | 7.9 | 4.5 | 4.9 |
| 174 | | 285 | 84.2 | 84.2 | 10.9 | 10.9 | 4.9 | 5.0 |
| 175 | | 273 | 83.5 | 82.8 | 11.4 | 11.6 | 5.1 | 4.9 |
| 176 | | 323 | 81.7 | 81.8 | 9.0 | 9.1 | 4.3 | 4.3 |
| 177 | | 267 | 80.9 | 81.1 | 7.9 | 8.0 | 5.2 | 5.4 |
| 178 | | 357/359 | 73.8 | 74.9 | 7.9 | 7.7 | 3.9 | 4.4 |
| 179 | | 337 | 81.9 | 81.1 | 9.3 | 9.3 | 4.1 | 4.7 |
| 180 | | 233 (M+-HCl) | 66.8 | 66.2 | 9.0 | 8.7 | 5.0 | 5.2 |
| 181 | | 371/373 | 74.3 | 74.9 | 8.1 | 9.1 | 3.8 | 4.3 |
| 182 | | 315/317 | 72.3 | 70.1 | 7.0 | 7.2 | 4.4 | 5.4 |
| 183 | | 301/303 | 71.6 | 71.6 | 6.7 | 6.8 | 4.6 | 5.1 |
| 184 | | 345/347 | 62.4 | 62.5 | 5.8 | 6.1 | 4.0 | 4.2 |
| 185 | | 315 | 87.6 | 87.1 | 8.0 | 7.9 | 4.4 | 4.5 |
| 186 | | 371 | 87.2 | 87.5 | 9.0 | 9.2 | 3.8 | 3.7 |
| 187 | | 257 | | | | | | |
| 188 | | 296 | 75.0 | 74.9 | 8.0 | 7.9 | 7.9 | 8.0 |
| 189 | 77-79 | 266 | 81.2 | 80.3 | 8.3 | 8.4 | 10.5 | 10.3 |
| 190 | | 313 | 84.3 | 82.1 | 11.3 | 10.8 | 4.4 | 4.5 |
| 191 | | 251 | 86.0 | 83.5 | 8.4 | 8.1 | 5.6 | 5.7 |

TABLE IA-continued

| Example No. | | M+ Found | Analysis % C Calc. | C Found | H Calc. | H Found | N Calc. | N Found |
|---|---|---|---|---|---|---|---|---|
| 192 | 49 | 251 | 86.0 | 86.3 | 8.4 | 8.7 | 5.6 | 6.0 |
| 193 | | 265 | 86.0 | 86.2 | 8.7 | 8.3 | 5.3 | 4.4 |
| 194 | | 285/287 | 75.6 | 75.8 | 7.1 | 7.4 | 4.9 | 4.9 |
| 195 | | 245 | 83.2 | 83.7 | 11.1 | 11.2 | 5.7 | 6.0 |
| 196 | | 307 | 85.9 | 85.1 | 9.5 | 9.4 | 4.6 | 4.6 |
| 197 | | 321 | 85.9 | 85.4 | 9.7 | 9.8 | 4.4 | 4.5 |
| 198 | | 341/343 | 77.3 | 75.2 | 8.3 | 8.1 | 4.1 | 4.0 |
| 199 | | 301 | 83.7 | 83.9 | 11.7 | 11.8 | 4.6 | 4.8 |
| 200 | | 301 | 83.7 | 83.9 | 11.7 | 11.8 | 4.6 | 4.8 |

EXAMPLE 201

The fungicidal activity of compounds of the invention was investigated by means of the following tests.

(a) Antisporulant activity against vine downy mildew (*Plasmopara viticola;* Pva)

The test is a direct antisporulant one using a foliar spray. The lower surfaces of leaves of whole vine plants (cv Cabernet Sauvignon) are inoculated by spraying with an aqueous suspension containing $10^4$ zoosporangia/ml 2 days prior to treatment with the test compound. The inoculated plants are kept for 24 hours in a high humidity compartment, then 24 hours at glasshouse ambient temperature and humidity. Infected leaves are sprayed on their lower surfaces with a solution of active material in 1:1 water/acetone containing 0.04% "TWEEN 20" (Trade Mark; a polyoxyethylene sorbitan ester surfactant). The spraying is carried out with a moving track sprayer giving an application rate of 1 kg/ha. After spraying, the plants are returned to normal glasshouse conditions for 96 hours and are then transferred to the high humidity compartment for 24 hours to induce sporulation, prior to assessment. Assessment is based on the percentage of the leaf area covered by sporulation compared with that on control leaves.

(b) Direct protectant activity against vine downy mildew (*Plasmopara viticola;* Pvp)

The test is a direct protectant one using a foliar spray. The lower surfaces of leaves of whole vine plants (cv Cabernet Sauvignon) are sprayed with the test compound at a dosage of 1 kilogram of active material per hectare using a track sprayer as described under (a), and after a subsequent 24 hours under normal glasshouse conditions the lower surfaces of the leaves are inoculated by spraying with an aqueous solution containing $10^4$ zoosporangia/ml. The inoculated plants are kept for 24 hours in a high humidity compartment, 5 days under normal glasshouse conditions and then returned for a further 24 hours to high humidity. Assessment is based on the percentage of leaf area covered by sporulation compared with that on control leaves.

(c) Direct protectant activity against vine grey mould (*Botrytis cinerea;* Bcp)

The test is a direct protectant one using a foliar spray. The lower surfaces of detached vine leaves (cv Cabernet Sauvignon) are sprayed with the test compound at a dosage of 1 kg/ha using a track sprayer as in (a). 24 hours after spraying the leaves are inoculated with droplets of aqueous suspension containing $10^5$ conidia/ml. After a further 5 days in high humidity the percentage of leaf area covered by disease is assessed.

(d) Activity against wheat leafspot (*Leptosphaeria nodorum;* Ln.)

The test is a direct therapeutic one, using a foliar spray. Leaves of wheat plants (cv Mardler), at the single leaf stage, are inoculated by spraying with an aqueous suspension containing $1\times10^6$ spores/ml. The inoculated plants are kept for 24 hours in a high humidity compartment prior to treatment. The plants are sprayed with a solution of the test compound at a dosage of 1 kilogram of active material per hectare using a track sprayer as described under (a). After drying, the plants are kept for 6–8 days at 20°–25° C. and moderate humidity, followed by assessment. Assessment is based on the density of lesions per leaf compared with that on leaves of control plants.

(e) Activity against barley powdery mildew (*Erysiphe graminis* f.sp. hordei; Eg)

The test is a direct therapeutic one, using a foliar spray. Leaves of barley seedlings, (cv. Golden Promise) are inoculated by dusting with mildew conidia one day prior to treatment with the test compound. The inoculated plants are kept overnight at glasshouse ambient temperature and humidity prior to treatment. The plants are sprayed with the test compound at a dosage of 1 kilogram of active material per hectare using a track sprayer as described under (a). After drying, plants are returned to a compartment at 20°–25° C. and moderate humidity for up to 7 days, followed by assessment. Assessment is based on the percentage of leaf area covered by sporulation compared with that on leaves of control plants.

(f) Activity against wheat brown rust (*Puccinia recondita;* Pr)

The test is a direct protectant one using a foliar spray. Wheat seedlings (cv Brigand) are grown to the 1–1½ leaf stage. The plants are then sprayed with the test compound at a dosage of 1 kg/ha using a track sprayer as described under (a). Test compounds are applied as solutions or suspensions in a mixture of acetone and water (50:50 v/v) containing 0.04% surfactant ("TWEEN 20" - Trade Mark).

18–24 hours after treatment, the seedlings are inoculated by spraying the plants from all sides with an aqueous spore suspension containing about $10^5$ spores/ml. For 18 hours after inoculation, the plants are kept in high humidity conditions at a temperature of 20°–22° C. Thereafter, the plants are kept in ambient glasshouse conditions, that is, in moderate relative humidity and at a temperature of 20° C.

The disease is assessed 10 days after inoculation on the basis of the percentage of the plant covered by sporulating pustules compared with that on the control plants.

(g) Activity against rice leaf blast (*Pyricularia oryzae* Po)

The test is a direct therapeutic one using a foliar spray. The leaves of rice seedlings (about 30 seedlings per pot) are sprayed with an aqueous suspension containing $10^5$ spores/ml 20-24 hours prior to treatment with the test compound. The inoculated plants are kept overnight in high humidity and then allowed to dry before spraying with the test compound at a dosage of 1 kilogram of active material per hectare using a track sprayer as described under (a). After treatment the plants are kept in a rice compartment at 25°-30° C. and high humidity. Assessments are made 4-5 days after treatment and are based on the density of necrotic lesions per leaf when compared with control plants.

(h) Activity against tomato early blight (*Alternaria solani;* As)

This test measures the contact prophylactic activity of test compounds applied as a foliar spray.

Tomato seedlings (cv Outdoor Girl) are grown to the stage at which the second true leaf is expanded. The plants are treated using a track sprayer as described under (a). Test compounds are applied as solutions or suspensions in a mixture of acetone and water (50:50 v/v) containing 0.04% surfactant ("TWEEN 20" - Trade Mark).

One day after treatment the seedlings are inoculated by spraying the leaf upper surfaces with a suspension of *A. solani* conidia containing $10^4$ spores/ml. For 3 days after inoculation plants are kept moist in a glasshouse compartment at or near 100% RH and 21° C. Thereafter plants are kept under humid, but not saturated, conditions. Disease is assessed 7 days after inoculation, based on the density and spread of lesions.

(i) Activity against wheat eyespot in-vitro (*Pseudocercosporella herpotrichoides;* PhI)

This test measures the in vitro activity of compounds against the fungus causing wheat eyespot.

The test compound is dissolved or suspended in acetone and is added to molten half strength Potato Dextrose Agar to give a final concentration of 100 ppm compound and 3.5% acetone. After the agar has set, plates are inoculated with 6 mm diameter plugs of agar/mycelium taken from a 14 day old culture of *P. herpotrichoides.*

Plates are incubated at 20° C. for 12 days and radial growth from the inoculation plug is measured.

(j) Activity against Fusarium in-vitro (Fusarium species; FsI)

This test measures the in vitro activity of compounds against a species of Fusarium that causes stem and root rots.

Compound is dissolved or suspended in acetone and added to molten half strength Potato Dextrose Agar to give a final concentration of 100 ppm compound and 3.5% acetone. After the agar has set, plates are inoculated with 6 mm diameter plugs of agar and mycelium taken from a 7 day old culture of Fusarium sp..

Plates are incubated at 20° C. for 5 days and radial growth from the plug is measured.

The extent of disease control in all the above tests is expressed as a rating compared with either an untreated control or a diluent-sprayed-control, according to the criteria:

0=less than 50% disease control
1=about 50-80% disease control
2=greater than 80% disease control The results of these tests are set out in Table II below:

TABLE II

| Compound | Fungicidal Activity | | | | | | | | | |
|---|---|---|---|---|---|---|---|---|---|---|
| Ex. No. | Pva | Pvp | Bcp | Ln | Eg | Pr | Po | As | PhI | FsI |
| 1 | | | | | 2 | | | | 2 | |
| 2 | | 1 | | | 1 | | | | 1 | 1 |
| 3 | | | | | 2 | | | | 2 | |
| 4 | | 1 | | | | | | | 1 | |
| 5 | | 1 | | | 1 | 1 | 1 | | 1 | |
| 6 | | | | | 1 | 1 | | | 2 | 1 |
| 7 | | 1 | 2 | | 2 | | | | 1 | |
| 8 | | 1 | | 1 | | | | | | |
| 9 | | 2 | | | | | | 1 | | |
| 10 | | | | | | 1 | | | | |
| 11 | 1 | | | | 2 | | | | | |
| 12 | | | | | 1 | | | | | |
| 13 | | | | 1 | 2 | 1 | | | 2 | |
| 14 | | | | | 2 | | | | 1 | |
| 15 | | | | | 2 | | | | 2 | |
| 16 | | | | | 1 | | | | 1 | |
| 17 | | | | | 1 | | | | 1 | |
| 18 | | | | | 1 | | | | | |
| 19 | | | | | 1 | | | | 1 | |
| 20 | 2 | 1 | | | | | | | 1 | |
| 21 | | | | | 2 | | | | 1 | |
| 22 | | | | | 1 | | 1 | | | |
| 23 | | 1 | | | 1 | | | 1 | | |
| 24 | | | | 1 | | | | | | |
| 25 | | | | | 2 | | | | 2 | |
| 26 | | 1 | | | 1 | | | | | |
| 27 | | 1 | | | 2 | | | | 1 | |
| 28 | | 1 | | | | 1 | | | 1 | |
| 29 | | | | 1 | 1 | | | | | |
| 30 | | 1 | | | 2 | 1 | | | 1 | 1 |
| 31 | | | | | 2 | 1 | | | 1 | 2 |
| 32 | | 1 | | | 2 | 2 | | | | 2 |
| 33 | | | | | 2 | | | | | |
| 34 | | 2 | | | 2 | | | | 1 | |
| 35 | | | | | 2 | | | | 1 | |
| 36 | | 1 | | | 2 | | | | | |
| 37 | 2 | 1 | | | 2 | | | | | |
| 38 | 2 | | | | 2 | | | | 1 | |
| 39 | 1 | 1 | | | 2 | | | | 1 | |
| 40 | | 1 | | | 1 | | | | 1 | |
| 41 | 1 | 1 | | | 2 | 1 | | | 2 | |
| 42 | | 2 | | | 2 | 1 | 1 | | 1 | |
| 43 | | 2 | | | 1 | 1 | | 1 | 2 | 1 |
| 44 | | | | 2 | 2 | | | | 1 | |
| 45 | | 1 | | 1 | 2 | | | | 1 | |
| 46 | | 1 | | | 2 | | 1 | | 1 | 1 |
| 47 | | 2 | | | 2 | 2 | | | 1 | 2 |
| 48 | | 1 | | | 2 | 2 | | | 2 | |
| 49 | | 1 | | | 2 | 2 | | | 1 | 1 |
| 50 | | | | | 2 | | | | 1 | |
| 51 | | 1 | | | 2 | | | | 1 | |
| 52 | | | | | 2 | 1 | | | 2 | 2 |
| 53 | | 1 | | 1 | 2 | 2 | | | 2 | |
| 54 | | 2 | | | | | | | | |
| 55 | | 2 | 1 | | 2 | | 1 | | 1 | 1 |
| 56 | | 2 | | | 1 | | | | | 1 |
| 57 | | 1 | | | 2 | | | | 1 | 1 |
| 58 | | 1 | | 1 | 2 | 2 | 1 | | 2 | 2 |
| 59 | | 1 | | | 2 | 1 | | | 2 | |
| 60 | | 1 | | | 2 | 1 | | | 2 | 2 |
| 61 | | 1 | | | 2 | 2 | | | 2 | |
| 62 | | 1 | | | 1 | | | | | |
| 63 | | 1 | | | 2 | 2 | 1 | | 2 | 2 |
| 64 | | 1 | | | 2 | | | | 1 | |
| 65 | | | | | 2 | | | | 1 | |
| 66 | | 1 | | | 2 | | | | 1 | |
| 67 | | 2 | 1 | | 1 | 2 | | | 1 | 1 |
| 68 | | 2 | | | 2 | 2 | | | 1 | |
| 69 | | 1 | | 1 | 2 | | | | 2 | |
| 70 | | 1 | | | 2 | | | | 2 | |
| 71 | | 2 | 1 | | 2 | | | | 1 | |

TABLE II-continued

| Compound Ex. No. | Fungicidal Activity | | | | | | | | | |
|---|---|---|---|---|---|---|---|---|---|---|
| | Pva | Pvp | Bcp | Ln | Eg | Pr | Po | As | Phl | Fsl |
| 72 | | | | | 2 | 1 | | | 2 | |
| 73 | | 2 | | | 2 | 1 | | | 2 | 1 |
| 74 | | 1 | | 1 | 2 | | | | | |
| 75 | | 1 | | | 2 | | | | 2 | 1 |
| 76 | | 1 | | | 2 | 2 | | | 2 | 1 |
| 77 | | 1 | | | 2 | | | | 1 | |
| 78 | | 1 | | | 2 | | | | 1 | |
| 79 | | | | | 2 | | | | 1 | |
| 80 | | 1 | 1 | | 2 | 1 | 1 | | 1 | |
| 81 | | | | | 2 | | | 1 | | |
| 82 | | | | | 2 | | 1 | | 2 | |
| 83 | | | | | 2 | 1 | | | 1 | 1 |
| 84 | | | | | 2 | | | | | |
| 85 | | 1 | 2 | | 2 | | | | | |
| 86 | | 1 | | | | 1 | | | 1 | 1 |
| 87 | | | | | 2 | 1 | 1 | | 1 | 1 |
| 88 | | 2 | 2 | | 2 | 1 | | 1 | 1 | 1 |
| 89 | | 1 | | | 2 | | | | 2 | |
| 90 | | 1 | | | 2 | | | | 1 | |
| 91 | | 1 | | | 2 | | | | 2 | |
| 92 | | | | | | | | | 1 | |
| 93 | | | | | 2 | | | | 1 | |
| 94 | | | | | 2 | 1 | | | 1 | |
| 95 | | 1 | | | 1 | | | | | |
| 96 | | | | 1 | 2 | 1 | | | 2 | |
| 97 | | 2 | | 1 | 2 | | | | 2 | |
| 98 | | | | | 2 | 1 | | | 1 | |
| 99 | | 1 | | | 2 | | | | 2 | |
| 100 | | | | 2 | 2 | 1 | | | 2 | 1 |
| 101 | | 1 | | 1 | 2 | 1 | | | | |
| 102 | | | | | 2 | 1 | | | 2 | |
| 103 | | 1 | | | 1 | | | | 1 | |
| 104 | | 1 | | | 2 | | | | 1 | |
| 105 | | 1 | | | 2 | 1 | | | 2 | |
| 106 | | 1 | | 1 | 2 | | | | 1 | |
| 107 | | | | | 2 | 1 | | | 1 | |
| 108 | | | | | 2 | | | | 1 | |
| 109 | | | | | 1 | | | | | |
| 110 | | | | 1 | 2 | 1 | 1 | | 2 | |
| 111 | | 1 | | | | | | | | |
| 112 | | | | | 2 | | | | 1 | |
| 113 | | 1 | | | 2 | | | | 2 | 1 |
| 114 | | 2 | | 1 | 2 | 1 | | | 2 | |
| 115 | | 2 | | | | | | | 1 | |
| 116 | | | | | 2 | 1 | | | 1 | |
| 117 | 1 | | | | | | | | 2 | 1 |
| 118 | | | | | 2 | | | | | |
| 119 | | 1 | | | 2 | | | | 2 | |
| 120 | | | | | | | | | 2 | |
| 121 | 1 | | | | | | | | 2 | |
| 122 | 2 | 1 | | 1 | 2 | 1 | | | 2 | |
| 123 | | | | | | | | | 2 | |
| 124 | | 1 | | | | | | | 2 | |
| 125 | | 1 | | | | | | | 1 | |
| 126 | | | | | 1 | | | | 1 | |
| 127 | | 1 | | | 2 | | | | 2 | |
| 128 | | | | | 1 | | | | | |
| 129 | | | | | 1 | | | | 1 | |
| 130 | | | | | 1 | | | | 1 | |
| 131 | 2 | 1 | | | | | | | 1 | |
| 132 | | | | | 2 | | | | 1 | |
| 133 | | | | | 2 | | | | | |
| 134 | | | | 2 | 2 | | | | 1 | |
| 135 | | 1 | | | 2 | | | | 2 | |
| 136 | | 1 | | | | | | | 1 | |
| 137 | | 1 | | | 1 | | | | 1 | |
| 138 | | 1 | | | | | | | 1 | |
| 139 | | 1 | | | 2 | | | | 1 | |
| 140 | | 1 | | | 2 | | | | 1 | |
| 141 | | | | | 2 | | | | 2 | |
| 142 | | 1 | | | 2 | 2 | | | 1 | |
| 143 | | 2 | 2 | 2 | 2 | 1 | | | 2 | |
| 144 | | | | | 2 | | | | 1 | |
| 145 | | | | 1 | 2 | | | | 1 | |
| 146 | | | 2 | | 1 | | | | 1 | |
| 147 | | 1 | 2 | | 2 | | | | 1 | |
| 148 | | 1 | 2 | | 2 | | | | 1 | 1 |
| 149 | | 1 | 2 | | 2 | 1 | | | 1 | |
| 150 | | | 2 | | 2 | | | | 2 | 1 |

TABLE II-continued

| Compound Ex. No. | Fungicidal Activity | | | | | | | | | |
|---|---|---|---|---|---|---|---|---|---|---|
| | Pva | Pvp | Bcp | Ln | Eg | Pr | Po | As | Phl | Fsl |
| 151 | | 1 | 2 | | | | | | | |
| 152 | | 1 | | 2 | 2 | 2 | | | 1 | 1 |
| 153 | | | | | 2 | 1 | | | 1 | |
| 154 | | 1 | | | 2 | | | | 1 | |
| 155 | | | | | | | | | 1 | |
| 156 | 1 | 1 | | | | | | | | 1 |
| 157 | | | | | 1 | | | | | 1 |
| 158 | | 1 | | | 1 | | | | 1 | |
| 159 | | 1 | | | 2 | | | | 2 | |
| 160 | | 1 | | | 2 | 2 | | | 2 | |
| 161 | 1 | | | | 1 | 1 | | | | |
| 162 | | 1 | | | | | | 1 | | |
| 163 | | 2 | | | 2 | 2 | | | 2 | 1 |
| 164 | | 1 | | | 1 | 1 | | | 1 | |
| 165 | | | | | 1 | 1 | | | 1 | |
| 166 | | 1 | | | | | | | | |
| 167 | | 1 | | | 1 | 1 | | | 2 | |
| 168 | | | | | 1 | | | | | |
| 169 | | 1 | | | 2 | 2 | | | 2 | |
| 170 | | | | | 2 | | | | | |
| 171 | | | | | 2 | 1 | | | 2 | |
| 172 | | | | | 2 | | | | 2 | |
| 173 | | | | | 2 | | | | 2 | |
| 174 | | | | | 2 | | | | 1 | |
| 175 | | | | | 2 | 1 | | | 2 | |
| 176 | | | | | 2 | | | | 1 | |
| 177 | | 1 | | | 1 | 1 | | | 1 | |
| 178 | | 1 | | | 2 | 1 | | | | |
| 179 | | 1 | 2 | | 2 | 1 | | | 2 | |
| 180 | | 1 | | | | 1 | | | | |
| 181 | 1 | 1 | | | | 1 | | | | |
| 182 | | 1 | | | 2 | | | | 2 | |
| 183 | 1 | | 2 | 1 | 2 | | | | 1 | |
| 184 | 1 | | | 1 | 2 | | | | 1 | |
| 185 | | | | | | | | | 2 | |
| 186 | | 1 | | | | | | 2 | | |
| 187 | | 2 | | | 1 | 1 | | | | |
| 188 | | 1 | | | | | | | | |
| 189 | | | | | | | | 1 | | |
| 190 | | 2 | 1 | | 1 | | | | 1 | |
| 191 | | 1 | | | | | | | | 1 |
| 192 | | | | | | | | | 1 | |
| 193 | 1 | | | | 1 | | | | 2 | |
| 194 | | 1 | | | 2 | | | | 2 | |
| 195 | 2 | 1 | | | | | | | 2 | |
| 196 | | 1 | | | 1 | 2 | | | 1 | |
| 197 | | 1 | | | 1 | 2 | | | 1 | |
| 198 | 1 | 1 | | | 2 | 2 | | | 1 | |
| 199 | | 2 | | | 2 | 2 | | | 2 | |
| 200 | | 2 | | | 2 | 2 | | | 2 | |

We claim:

1. A method of combating fungus at a locus which comprises treating the locus with a fungicidally effective amount of a compound of the formula

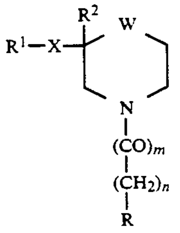

(I)

or an acid-addition salt or metal salt complex thereof, in which R represents a hydrogen atom or an optionally substituted alkyl, alkenyl, alkynyl, alkoxy, cycloalkyl, phenyl, naphthyl, phenylcarbonyl, naphthylcarbonyl, and thienyl; $R^1$ represents an optionally substituted alkyl, phenyl, benzyl or cycloalkyl group; $R^2$ represents a hydrogen atom or an optionally substituted alkyl group; W represents $-CH_2-$; X represents $-CH_2-$; $-CH_2CH_2-$, $-O-$ or a single chemical bond; m is 0 or 1 and n represents an integer from 0 to 3.

2. A method according to claim 1 in which R represents a hydrogen atom or a $C_{1-12}$ alkyl, $C_{2-6}$ alkenyl, $C_{2-6}$ alkynyl, $C_{1-6}$ alkoxy, $C_{3-8}$ cycloalkyl, phenyl, naphthyl, or phenylcarbonyl, each group being optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino, formyl, $C_{1-4}$ alkoxycarbonyl, carboxyl, phenyl and halophenoxy groups.

3. A method according to claim 1 in which $R^1$ represents a phenyl, benzyl or $C_{3-8}$ cycloalkyl group, each group being optionally substituted by one or more substituents selected from halogen atoms, nitro, cyano, hydroxyl, $C_{1-4}$ alkyl, $C_{1-4}$ haloalkyl, $C_{1-4}$ alkoxy, $C_{1-4}$ haloalkoxy, amino, $C_{1-4}$ alkylamino, di-$C_{1-4}$ alkylamino, formyl, $C_{1-4}$ alkoxycarbonyl and carboxyl groups.

4. A method according to claim 1 in which R represents a hydrogen atom, methyl, ethyl, propyl, butyl, pentyl, hexyl, heptyl, octyl, nonyl, decyl, undecyl, dodecyl, hydroxymethyl, hydroxyethyl, hydroxypropyl, hydroxybutyl, ethoxyethyl, ethoxymethyl, diethoxyethyl, diethoxymethyl, ethoxycarbonylmethyl, dichlorophenoxyhydroxypropyl, ethenyl, propenyl, ethynyl, propynyl, butoxy, methoxyethoxy, cyclopentyl, cyclohexyl, phenyl, fluorophenyl, chlorophenyl, dichlorophenyl, bromophenyl, nitrophenyl, cyanophenyl, hydroxyphenyl, methylphenyl, butylphenyl, methoxyphenyl, aminophenyl, biphenylyl, naphthyl, hydroxynaphthyl, chlorophenylcarbonyl, or thienyl; $R^1$ represents a phenyl, chlorophenyl, methylphenyl, propylphenyl, butylphenyl, methoxyphenyl, fluorobenzyl or cyclohexyl group; and $R^2$ represents a hydrogen atom or methyl group.

5. A method according to claim 1 in which said locus is treated with said compound in the form of a fungicidal composition which comprises at least two carriers, at least one of which is a surface-active agent.

6. A method according to claim 1 in which the locus comprises plants subject to or subjected to fungal attack, seeds of such plants or the medium in which the plants are growing or are to be grown.

7. A method according to claim 1 wherein said compound is defined by formula I with the provisos that (i) when m is 1, n is 2, R is methyl, $R^2$ is hydrogen and X is $-CH_2CH_2-$, then $R^1$ is not an unsubstituted benzyl group; and (ii) when m is 1, n is 1, R is 5-chloro-2-oxobenzothiazolin-3-yl, $R^2$ is hydrogen and X is a single bond, then $R^1$ is not a hydroxymethyl or 3-hydroxypropyl group.

* * * * *